United States Patent [19]

Chandler et al.

[11] Patent Number: 4,864,845
[45] Date of Patent: Sep. 12, 1989

[54] ELECTRONIC FIELD PERMEAMETER

[75] Inventors: Mark A. Chandler, Madison, Wis.; David J. Goggin, Austin, Tex.; Patrick J. Horne, Austin, Tex.; Gary G. Kocurek, Roundrock, Tex.; Larry W. Lake, Austin, Tex.

[73] Assignee: Board of Regents University of Texas System, Austin, Tex.

[21] Appl. No.: 102,555

[22] Filed: Sep. 29, 1987

[51] Int. Cl.$^4$ ............................................. G01N 15/08
[52] U.S. Cl. ......................................... 73/38; 73/155; 364/422
[58] Field of Search ........................... 73/155, 37, 38; 364/558, 422

[56] References Cited

U.S. PATENT DOCUMENTS

| | | | |
|---|---|---|---|
| 3,504,527 | 4/1970 | Marshall | 73/38 |
| 3,808,876 | 5/1974 | Kershaw | 73/38 |
| 4,198,854 | 4/1980 | Washington et al. | 73/38 |
| 4,462,248 | 7/1984 | Cronshaw | 73/38 |
| 4,542,343 | 9/1985 | Brown | 324/307 |
| 4,555,934 | 12/1985 | Freeman et al. | 73/38 |
| 4,561,289 | 12/1985 | Jones | 73/38 |
| 4,573,342 | 3/1986 | Jones | 73/38 |
| 4,625,544 | 12/1986 | Hi-Hwa Yuan et al. | 73/38 |
| 4,628,468 | 12/1986 | Thompson et al. | 364/556 |
| 4,643,019 | 2/1987 | Jones | 73/38 |
| 4,644,283 | 2/1987 | Vinegar et al. | 324/376 |
| 4,648,261 | 5/1987 | Thompson et al. | 73/38 |
| 4,671,100 | 6/1987 | Doussiet | 73/38 |
| 4,679,421 | 7/1987 | Barree | 73/38 |
| 4,679,422 | 7/1987 | Rubin et al. | 73/38 |
| 4,701,861 | 10/1987 | Kauke | 73/38 X |
| 4,718,270 | 1/1988 | Storr | 73/38 |

OTHER PUBLICATIONS

Goggin et al., "Patterns of Permeability in Eolian Deposits", SPE/DOI Fifth Symposium on Enhanced Oil Recovery, Tulsa, Oklahoma (Apr. 20–23, 1986).
Eijpe and Weber, "Minipermeameters for Consolidated Rock and Unconsolidated Sand", AAPG Bull., vol. 55, No. 2 (Feb. 1971) pp. 307–309.
*Omega Pressure and Strain Measurement Handbook and Encyclopedia*, pp. B–11, D–33, D–44 (1984).
*Omega Flow Measurements and Control Handbook and Encyclopedia*, pp. D–17, D–18 (1984).

*Primary Examiner*—Eugene R. LaRoche
*Assistant Examiner*—Seung Ham
*Attorney, Agent, or Firm*—Arnold, White & Durkee

[57] ABSTRACT

For making rapid, non-destructive permeability measurements in the field, a portable minipermeameter of the kind having a manually-operated gas injection tip is provided with a microcomputer system which operates a flow controller to precisely regulate gas flow rate to a test sample, and reads a pressure sensor which senses the pressure across the test sample. The microcomputer system automatically turns on the gas supply at the start of each measurement, senses when a steady-state is reached, collects and records pressure and flow rate data, and shuts off the gas supply immediately after the measurement is completed. Preferably temperature is also sensed to correct for changes in gas viscosity. The microcomputer system may also provide automatic zero-point adjustment, sensor calibration, over-range sensing, and may select controllers, sensors, and set-points for obtaining the most precise measurements. Electronic sensors may provide increased accuracy and precision. Preferably one microcomputer is used for sensing instrument control and data collection, and a second microcomputer is used which is dedicated to recording and processing the data, selecting the sensors and set-points for obtaining the most precise measurements, and instructing the user how to set-up and operate the minipermeameter. To provide mass data collection and user-friendly operation, the second microcomputer is preferably a lap-type portable microcomputer having a non-volatile or battery-backed CMOS memory.

5 Claims, 13 Drawing Sheets

| ASCI CODE | PARAMETERS | COMMAND PROCEDURE |
|---|---|---|
| "G" | | RESET |
| "H" | | TRIGGER BEEPER |
| "I" | | CHECK AND TRANSMIT STATUS |
| "J" | N  X | SET MASS FLOW FOR CONTROLLER N TO X |
| "K" | N  X | SET VOLTAGE FOR SENSOR N TO X |
| "L" | N | READ MASS FLOW FROM CONTROLLER N |
| "M" | N | READ PRESSURE FROM SENSOR N |
| "N" | CODE NUMBER | PROGRAM EEROM |
| "O" | CODE NUMBER | EXECUTE EEROM CUSTOM PROGRAM |

—70

ELECTRONIC FIELD PERMEAMETER

The United States government may have rights in this invention pursuant to a funding arrangement with the Department of Energy.

BACKGROUND OF THE INVENTION

1. Field of the Invention

This invention relates to a field instrument for directly measuring the permeability of rock in situ.

2. Description of the Related Art

Permeability is an important formation characteristic that indicates how fast oil or gas may flow from an oil or gas bearing formation. Moreover, permeability is the only elementary rock property directly related to fluid flow, and permeability cannot be accurately estimated from other rock properties. Accurate measurement of rock permeability is difficult and requires the measurement or determination of fluid flow responsive to a pressure differential.

Two methods have commonly been used to measure rock permeability. One method obtains permeability of a formation by monitoring changes in the pressure of a borehole as fluid is pumped out. This method is useful for measuring the permeability of subsurface rocks in situ. Its disadvantage is that only an average permeability is obtained, leaving detailed permeability structures within the formation unrevealed. A second commonly used method requires that a plug be drilled from the formation. The plug is placed in a rubber sleeved core-plug holder known as a "Hassler-sleeve" and is sealed in place by a confining pressure applied to the outside of the sleeve. A pressure difference is applied across the length of the plug to induce fluid flow through the plug. The rate of flow and the pressure difference are measured, and the permeability is computed by applying a mathematical formula known as Darcy's law. This approach is described, for example, in Freemann et al. U.S. Pat. No. 4,555,934 and Jones et al. U.S. Pat. No. 4,573,342. Although this approach allows for more detailed studies of formation permeability, it is time consuming, it does not measure permeability in situ, and it is destructive to samples.

An instrument known as a mini-permeameter has been used for non-destructive measurement of rock permeability. As described in Eijpe and Weber, "Minipermeameters for Consolidated Rock and Unconsolidated Sand," AAPG Bull., Vol. 55, No. 2 (February 1971) p. 307–309, the instrument consists essentially of a narrow tube which is pressed with a controlled force against a flat, clean rock surface. Air is forced from the tube through the pores and flows out around the tube. A rubber ring at the tube's tip prevents leakage between the tip and the rock surface. A constant pressure drop is applied, and the air-flow rate is measured with a rotameter unit. The permeability of the sample is derived from this flow rate and the applied pressure. For field work, the pressurized air is supplied by a cylinder of compressed air or a small compressor. As further described in Goggin et al., "Patterns of Permeability in Eolian Deposits," SPE/DOI Fifth Symposium on Enhanced Oil Recovery, Tulsa, Okla. (April 20–23), 1986, the injection tip is pressed against an outcrop surface after the top $\frac{1}{4}$ cm of each measurement site is chipped away. The gas flow rate is estimated by a series of rotameters which are selected to accurately cover a wide range of possible rates. An estimate of the permeability may be obtained by calibrating the minipermeameter flow rate for various core plug samples of known permeability.

Operation of the minipermeameter in the field has been a laborious task prone to frequent error. To obtain the permeability of a rock formation in situ, measurements are taken at a large number of test sites at spaced intervals in an array or grid. Although the sensing of permeability occurs rapidly at each test site, the overall process requires a considerably greater amount of time for leveling the rotameters, monitoring the flow rate, adjusting pressure, and recording the field measurements. Also, bulky cylinders or an air compressor is needed to supply the relatively large amount of air required for sensing permeability at a large number of test sites.

SUMMARY OF THE INVENTION

Accordingly, the primary object of the invention is to provide a field permeameter capable of more rapid and precise operation.

Another object is to eliminate operator errors during the use of a minipermeameter.

Still another object is to eliminate errors during the recording and processing of minipermeameter data.

Yet another object of the invention is to provide a field permeameter which is especially compact, lightweight, and durable for use at remote field sites.

Moreover, another object of the invention is to provide a minipermeameter for field use which requires a minimal amount of pressurized gas for performing measurements at a multiplicity of test sites.

Briefly, in accordance with the invention, a mini-permeameter has a microcomputer system which operates a flow controller to precisely regulate gas flow rate to a test sample, and reads a pressure sensor which senses the pressure across the test sample. The microcomputer system automatically turns on the gas supply at the start of each measurement, senses when a steady-state is reached, collects and records pressure and flow rate data, and shuts off the gas supply immediately after the measurement is completed. Preferably temperature is also sensed to correct for changes in gas viscosity. The microcomputer system may also provide automatic zero-point adjustment, sensor calibration, over-range sensing, and may select controllers, sensors, and set-points for obtaining the most precise measurements. Electronic sensors may provide increased accuracy and precision.

Preferably one microcomputer is used for sensing, instrument control and data collection, and a second microcomputer is used which is dedicated to recording and processing the data, selecting the sensors and set-points for obtaining the most precise measurements, and instructing the user how to set-up and operate the minipermeameter. To provide mass data collection and user-friendly operation, the second microcomputer is preferably a lap-type portable microcomputer having a non-volatile or battery-backed CMOS memory. For the flexibility of interfacing the instrument control computer to various kinds of computers, ASCII codes convey data, control commands, and error signals over a standard RS232 serial link. For customizing the instrument control computer, it is provided with an EEROM instruction memory which can be automatically reprogrammed in response to a command received over the serial link.

BRIEF DESCRIPTION OF THE DRAWINGS

Other objects and advantages of the invention will become apparent upon reading the following detailed description and upon reference to the drawings in which.

Figure 1:
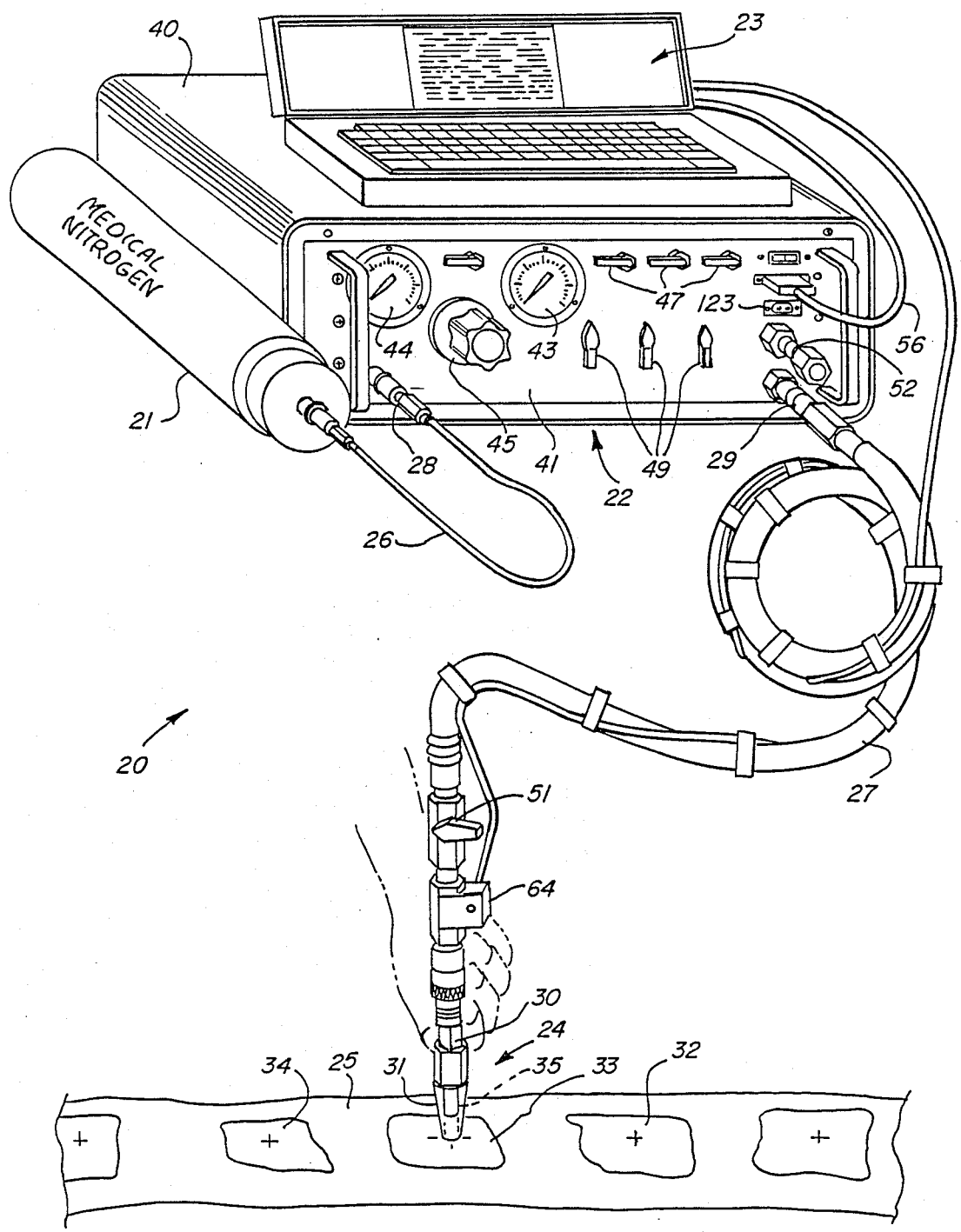
FIG. 1 is a perspective view of an electronic field permeameter of the present invention.

While the invention is susceptible to various modifications and alternative forms, a specific embodiment thereof has been shown by way of example in the drawings and will herein be described in detail. It should be understood, however, that it is not intended to limit the invention to the particular form disclosed, but on the contrary, the intention is to cover all modifications, equivalents, and alternatives falling within the spirit and scope of the invention as defined by the appended claims.

DESCRIPTION OF THE PREFERRED EMBODIMENT

Turning now to the drawings, there is shown in FIG. 1 an electronic field permeameter generally designated 20 in accordance with the present invention. The electronic field permeameter (EFP) is a portable device that measures the flow rate and injection pressure of a gas to determine permeability. The EFP includes a source of pressurized gas 21, a set of flow rate and pressure monitoring instruments 22, a portable microcomputer 23 for data collection and supervisory control, and a gas injection tip generally designated 24 which is pressed against the surface of a rock 25 to be tested. Preferably the gas supply 21 is provided by nitrogen in a medical "E-size" tank, because nitrogen is pure, inexpensive, and relatively safe. The tank 21 is portable and lightweight (15 pounds) and will hold 22 liters of nitrogen at 2200 psig. The tank 21 is connected to the flow rate and pressure monitoring instruments 22 via an inlet line 26, and an outlet line in the form of a flexible filling-station style air hose 27 conveys the nitrogen from the instruments 22 to the injection tip 24. The hose 27 remains flexible in adverse weather conditions and is very durable in the field. When measuring low permeability samples, however, it is preferable to use smaller tubing such as ⅛ inch Teflon tubing in place of the hose in order to achieve steady state flow more rapidly. For rapid assembly, quick-connect fittings 28, 29 connect the inlet and outlet lines 26, 27 with the instruments 22. The injection tip 24 is also attached to the hose 27 with a quick-connect fitting 30 so that tips of varying styles and diameters are easily interchanged.

The injection tip 24 includes a silicon rubber seal 31 to reduce leakage between the tip and any irregularities in the surface of the rock 25. For outcrop studies, such surface irregularities occur when a weathering layer of the outcrop is chipped away at regular intervals 32, 33, 34 to expose fresh surfaces which provide a permeability more representative of the bulk of the rock formation. As shown in FIG. 1, the silicon rubber seal 31 is a number 00 silicone rubber stopper commonly used for closing test tubes. Such stoppers are readily available, for example from Curtin-Mathuson Scientific, 9999 Veteran's Memorial Drive, Houston, Tex. A cork bore is used to form a central ¼ inch diameter hole so that the stopper 31 may removably seat on a ¼ inch outer diameter nipple 35 formed on the injector 24. Therefore, the silicon rubber seal 31 as well as the injection tip 24 is readily interchangeable for specific requirements, such as testing small samples.

In accordance with an important aspect of the present invention, the flow rate and pressure monitoring instruments 22 include computer controlled mass flow controllers and pressure sensors in order to establish and precisely measure the flow of gas through the test sample and to measure the pressure difference across the sample. The mass flow controllers and the pressure sensors are enclosed within a protective instrument box 40 which mates with a weather-tight cover (not shown) which fits over a front control panel 41. The instrument box 40 is slightly larger than a briefcase, and together with the flow rate and pressure monitoring instruments weighs approximately 40 pounds. The flow rate controlling and pressure monitoring instruments need not be leveled so that the instrument box 40 may be placed in any convenient position during the measurement process. For overland transport, the instrument box 40 is readily attached to a backpack frame (not shown).

Figure 2:
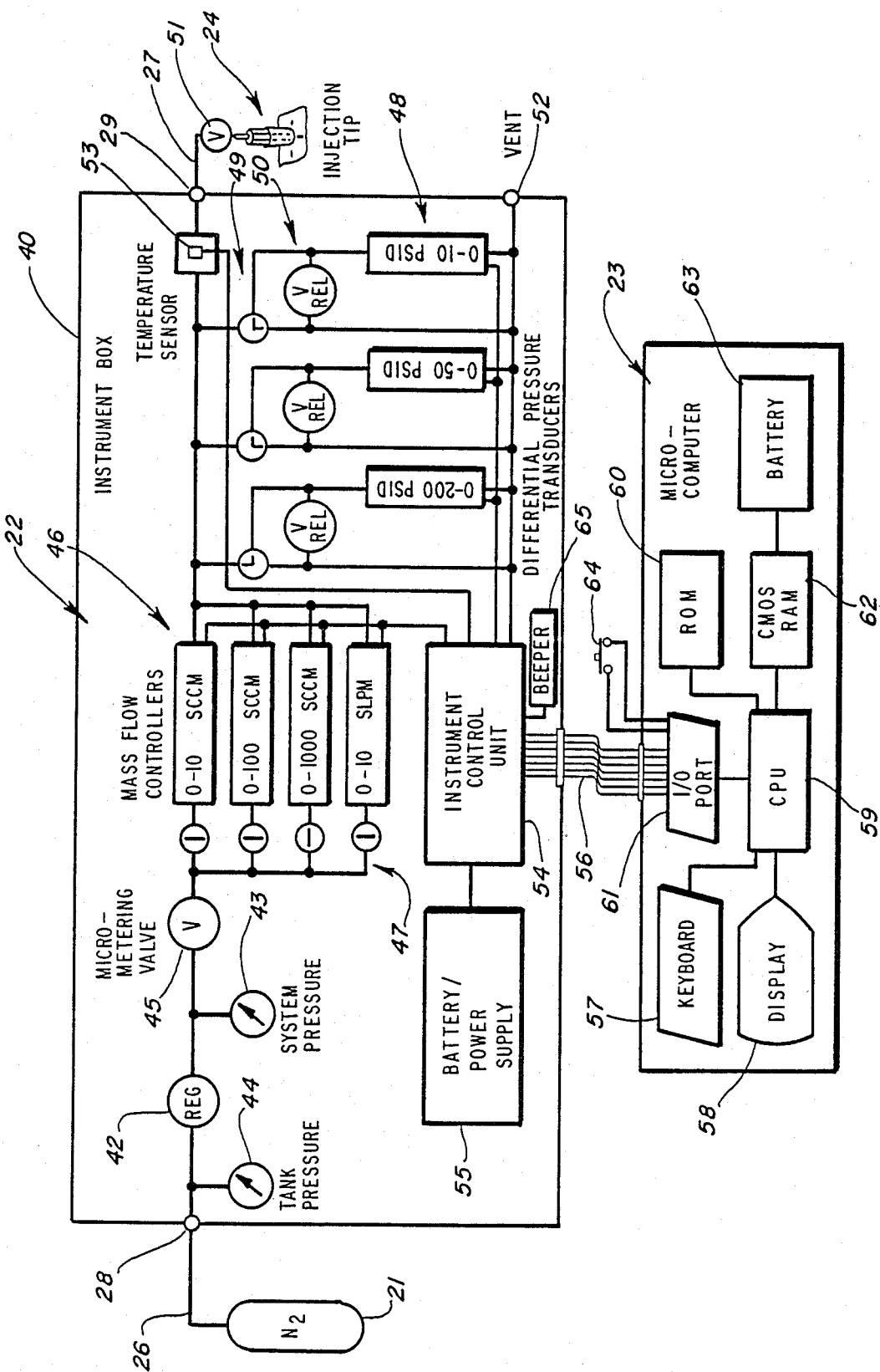
FIG. 2 is a schematic diagram of the electronic field permeameter of FIG. 1.

Turning now to FIG. 2, there is shown a schematic diagram including the flow rate and pressure monitoring instruments 22 inside the instrument box 40. To provide a relatively constant pressure supply of gas, the gas flows from the tank 21 through a two-stage pressure regulator 42 which can supply a system pressure of anywhere from 0 to 150 psi, depending upon an adjustment. The regulator 42 is preferably a model ESG 752 sold by Veriflo Co., P.O. Box 4034, 250 Canal Blvd., Richmond, Calif. 94804-0034. For most applications the regulator is adjusted to provide a constant 30 psi system pressure, as indicated by a standard dial-type pressure gauge 43. A second dial-type pressure gauge 44 is provided to indicate the tank pressure and thereby indicate the amount of gas remaining in the tank 21.

For measuring very low permeabilities, it is preferable to provide a gas supply that has a generally constant flow rate rather than a constant pressure. In these cases the user may restrict the flow of gas from the regulator 22 by selectively closing a micro-metering valve 45.

The micrometering valve is preferably a NUPRO "S" series valve, sold by NUPRO, 4800 East 345 Street, Willoughby, Ohio 44094.

To precisely regulate and measure the flow of gas, the instruments 22 preferably include four mass flow controllers generally designated 46 for the respective ranges of 0-10 sscm, 0-100 sscm, 0-1000 sscm, and 0-10 slpm. The mass flow controllers are preferably Datametrics model 825 sold by Dresser Industries, 340 Fordham Road, Wilmington, Mass. 01887. These mass flow controllers provide +/−1% full scale accuracy with +/−0.25% repeatability. Such flow controllers include an electromagnetically actuated low rate control valve for regulating the flow and a mass flow sensor for sensing the rate of flow.

For performing a permeability measurement, only one of the mass flow controllers 46 is operated. For this purpose, electrical power is applied to a selected one of the mass flow controllers, and the supply of power to the other mass flow controllers is shut off. When the supply of power to a mass flow controller is shut off, the electromagnetically actuated control valve in the controller closes to entirely stop the flow of gas through the controller. Moreover, to conserve the supply of pressurized gas, the supply of power to all of the mass flow controllers is preferably shut off during inactive intervals between successive permeability measurements. As a safety precaution and also to isolate a defective controller, a respective one of four plug valves 47 is connected in series with each of the mass flow controllers 46.

To measure the pressure of the gas applied to the test sample, the instruments 22 include a set of three pressure transducers 48 covering respective ranges of 0-10 psid, 0-50 psid, and 0-200 psid. The pressure sensors have an accuracy of +/−0.1% full scale, and are preferably model TJE wet/dry differential pressure sensors sold by Sensotec, 1200 Chesapeake Avenue, Columbus, Ohio 43212. Due to their sensitivity, the pressure sensors 48 can withstand only a limited range of overpressure without suffering permanent damage. The pressure sensors 48 typically can withstand a pressure of 250% of their sensing range. Therefore, in the case of the 0-50 psid and 0-100 psid sensors, excessive pressures could occur during operation of the instrument. Moreover, an excessive pressure could be applied to the 0-200 psid sensor in the event of a malfunction of the regulator 42.

To prevent damage to the sensors 48 during overpressure conditions, there are provided respective 3-way valves 49 to selectively remove the pressure sensors 48 from the gas supply and also to equalize the pressure across the pressure sensors. Although these 3-way valves could be solenoid operated to automatically remove and bypass each pressure sensor in the event of the respective pressure range being exceeded, it is believed that the reliability of such solenoid-operated valves is not sufficiently high to protect the relatively expensive pressure sensors 48. Therefore, the 3-way valves 49 are preferably manually-operated valves. To guard against an operator error in setting these valves 49, there are provided respective pressure relief valves 50 to prevent an excessive pressure from being applied across each of the pressure sensors 48. The pressure relief valves, for example, are adjusted to open at 20 psid, 100 psid, and 230 psid.

The pressure relief valves are, for example, NUPRO in-line adjustable relief valves sold by NUPRO, 4800 East 345 Street, Willoughby, Ohio 44094. The manually operated 3-way valves 49, as well as the plug valves 47, are available from Whitney, 318 Bishop Road, Highland Heights, Ohio 44143. The valves and transducers are connected using copper tubing and swage lock connections sold by Crawford Fitting Co., 29500 Solon Road, Solon, Ohio 44139. For safety purposes, a manually operated valve 51 is also provided near the injection tip 24 so as to prevent the possibility of a sudden unexpected blast of gas from the injection tip.

Although the flow control and pressure sensing instruments 22 in the instrument box 40 are primarily intended for use as a field permeameter according to the present invention, they could also be used for the measurement of permeability of core plugs placed in a "Hassler-sleeve" core-plug holder. For this purpose, the pressure transducers 48 are differential pressure transducers vented to a common vent connection 52. Therefore, for the "Hassler-sleeve" measurements, the outlet connection 27 and the vent connection 52 are connected to the opposite ends of the core-plug holder.

A parameter affecting the precision and accuracy of the mass flow controllers 46 and the differential pressure transducers 52 is temperature. Moreover, the temperature of the gas flowing through the test sample affects the measurement of permeability due to a slight increase in gas viscosity with increasing temperature. Therefore, it is desirable to provide a temperature sensor 53 in the instrument box 40 and in particular it is desirable to locate such a temperature sensor in the gas flow just before the gas leaves the outlet connector 27. For this purpose a solid state temperature sensor 53 is disposed in the gas line near the outlet 27. Since the effect of temperature on the permeability measurements is very slight, it is not necessary to use a particularly accurate temperature sensor, although the temperature sensor should have a rather fast response due to the fact that the temperature of the gas may drop quickly in the event of a sudden increase in the gas flow rate. A solid state temperature sensor is suitable, such as part number AD590 sold by Omega Engineering, Inc., 1 Omega Drive, Box 4047, Stamford, Conn. 06907. Such a solid state temperature sensor operates off a 5 volt supply and converts absolute temperature to a proportional output current. No linearization, amplification or cold junction compensation is required. An output current of one microamp per degree Kelvin is fed to a one kilo-ohm load resistor to provide a voltage indication of one millivolt per degree Kelvin.

For operation of the mass flow controllers 46, the temperature sensor 53 and the pressure sensors 48, the instrument box 40 preferably includes an instrument control unit 54 including a microcomputer. The instrument control unit 54 is powered by a battery or power supply 55. By providing an instrument control unit 54 with a microcomputer in the instrument box 40, the instruments are readily controlled by an external microcomputer 23 by passing elementary commands over a serial link 56. The serial link 56 preferably conforms to the RS232 standard, so that a large variety of external microcomputers 23 are readily used to control the instruments in the instrument box 40.

For field use, preferably the microcomputer 23 is a Tandy Model 200 lap-top computer. The microcomputer 23 includes a keyboard 57 and a liquid crystal display 58 for communicating with the user. The microcomputer also has a central processing unit 59 that executes elementary procedures stored in a read only memory 60 for receiving data from the keyboard 57, displaying messages on the display 58, and communicating over the serial link 53 via an input/output port 61. For executing user supplied programs, the microcomputer 23 has a CMOS random access memory 62 that is loaded with the user supplied program which is entered via the keyboard 57 or from a tape recorder (not shown) that may be connected to the input/output port 61. The random access memory 62 is powered by a battery 63 at all times, so that even when the central processing unit 59 is shut off, program and data are retained in the random access memory 62.

As will be further described below, the microcomputer 23 can be programmed to operate the instruments 22 to collect, process and record mass flow and pressure data for determining permeability. In the field, the data and the calculated permeability are stored in the random access memory 62. The Tandy Model 200 lap-top computer, for example, has up to 72K bytes of random access storage which is sufficient for storing all of the data to be collected in a single day's work. The data could be transferred to magnetic tape using a tape recorder, but it is contemplated that after each day's work in the field, the serial link 56 of the microcomputer would be connected to a telephone modem so that the data stored in the random access memory 62 would be transmitted to a mainframe computer for centralized data storage.

For performing a permeability measurement at a test site, the microcomputer 23 is preferably programmed to instruct the instrument control unit 54 to operate the mass flow controllers 46 to regulate a predetermined amount of gas flow to the test sample, and transmit back to the microcomputer 23 the actual mass flow and the pressure sensed by the pressure sensors 48. Preferably this measurement process starts when the user activates a push-button switch 64 which is mounted near the injector tip 24 (see FIG. 1). The push-button switch 64 is wired to the "light pen" input to the I/O port 61 of the microcomputer 32. In response to closure of the switch 64, the microcomputer 23 in cooperation with the instrument control unit 54 automatically turns on the gas supply, senses when a steady-state is reached, collects and records the pressure and flow rate data, and shuts off the gas supply immediately after the measurement is completed. At the end of the measurement process, the microcomputer 23 sends a command to the instrument control unit 54 for activating a beeper 65 in the instrument box 40. Upon hearing the beeper, the operator knows that the measurement for the current test site has been completed so that the injection tip 24 can be moved to another test site. (See FIG. 1).

Figures 3, 4:
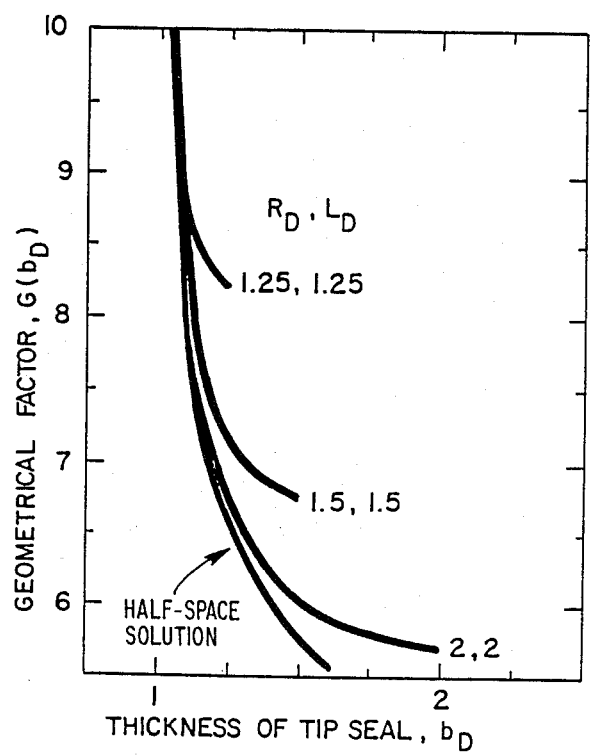
FIG. 3 is a table showing the control commands that are executed by a control unit of the electronic field permeameter.
FIGS. 4, 5 and 6 are graphs for determining a geometrical factor which is used to represent the geometry of the injector tip and the rock sample in the calculation of permeability.

Turning now to FIG. 3, there is shown a table generally designated 70 of a set of elementary commands that are transmitted by the microcomputer 23 over the serial link 56 to the instrument control unit 54. So that the instrument control unit may be interfaced to virtually any kind of computer, the data exchanged over the serial link 56 includes only alphabetic letters and decimal digits. The digits 0–9 and the letters A–F are reserved to represent hexadecimal numbers. The letters G–O represent elementary commands. The other letters represent error codes which are transmitted by the instrument control unit 54 back to the microcomputer 23 in the event of an error condition, as further described below.

When the electronic field permeameter is first turned on, the microcomputer 23 transmits a "G" command to reset the instrument control unit and thereby turn off all of the sensors and shut off the flow of gas. This reset command is also used after each measurement in order to conserve the supply of pressurized gas. A command "H" is transmitted to trigger the beeper 65 at the end of each measurement. A command "I" is transmitted to obtain the status of the instruments 22 in the instrument box 40. In response to the "I" command, the instrument controller 54 measures the power supply voltages and the temperature and transmits these data back to the microcomputer 23.

In order to turn on the flow of gas to perform a permeability measurement, the microcomputer 23 transmits a "J" command followed by a decimal digit "N" which designates one of the four mass flow controllers 46 to be turned on, and also transmits a hexadecimal number "X" designating the mass flow set point for the selected controller. Similarly, to turn on a selected one of the pressure sensors 48, the microcomputer 23 transmits a "K" command followed by a digit "N" indicating a selected one of the pressure sensors and a hexadecimal number "X" specifying a command voltage to be sent to the selected pressure sensor. To read the mass flow from the selected controller, the microcomputer 23 transmits an "L" command followed by the digit "N" specifying the selected controller. Similarly, to read the pressure from the selected sensor, the microcomputer 23 transmits the command "M" followed by the digit "N". During the measurement process, the microcomputer successively obtains mass flow and pressure values at periodic intervals, such as 20 times a second, until the mass flow and pressure values stabilize, indicating a steady-state. From the steady-state values, the microcomputer 23 calculates the permeability of the test sample.

It should be noted that the above-described commands in the table 70 of FIG. 3 represent a very elementary level of control for the instruments 22 in the instrument box 40. The user, therefore, may wish to program the instrument control unit 54 to recognize more sophisticated commands tailored to more specific or varied applications. For this purpose, the instrument control unit 54 may be provided with electrically erasable read only memory (EEROM) which is easily erased and reprogrammed with a customized program to suit the more specific or varied applications. As further described below, the instrument control unit 54 preferably recognizes elementary commands allowing the user to download and then execute a custom program transmitted by the microcomputer 23 via the serial link 56 to the EEROM in the instrument control unit 54. For this purpose the instrument control unit 54 recognizes a command "N" followed by a code number or password instructing the instrument control unit 54 to receive a program from the microcomputer 23 and to load that program into the EEROM. Moreover, the instrument control unit 54 recognizes a command "O" followed by a code number instructing the instrument control unit to execute the custom program having been loaded into the EEROM. The code number is required in each case as a safety precaution so that reprogramming of the EEROM and execution of a custom program occurs only when the "N" or "O" commands are followed by the proper code number. Therefore, reprogramming of the instrument control unit 54 will not occur inadvertently.

As described above, steady-state mass flow and pressure values are obtained in order to calculate the permeability of the test sample. In general, permeability is calculated by applying a form of Darcy's law as follows:

$$k_{gas} = \frac{q_1 u_{gas} P_1}{aG(P_1^2 - P_2^2)/2}$$

where
$k_{gas}$=the permeability in Darcies
$q_1$=flow rate in cm /sec,
$P_1$ and $P_2$=measured tip and atmospheric pressures, respectively, in atmospheres,
$u_{gas}$=viscosity of the gas in centipoises and
a=internal radius of the tip seal in centimeters.

The factor G is a geometrical factor which depends upon the particular shape of the injection tip and the dimensions of the test sample. In order to calculate the value of the geometric factor G it is assumed that the seal between the injection tip and the test sample is a ring having an internal radius of a and an external radius of b. Similarly, it is assumed that the test sample is in the form of a cylindrical core having a radius $R_c$ and a length $L_c$, and it is further assumed that the tip seal is coaxial with the axis of this core sample. For the case of an outcrop as shown in FIG. 1, the values $R_c$ and $L_c$ are assumed to take on very large or infinite values. By defining dimensionless geometrical parameters $b_D$, $R_D$, and $L_D$, then the geometrical factor G can be analytically expressed as:

$$G(b_D, R_D, L_D) = 2\pi \int_0^1 \left(\frac{\partial m_D}{\partial z_D}\right)_{z_D=0} r_D dr_D$$

where
$b_D$=b/a, ratio of external to internal tip seal radius,
$R_D$=$R_{core}$/a, ratio of core radius to internal tip seal radius and
$L_D$=$L_{core}$/a, ratio of core length to internal tip seal radius.

Figure 6:
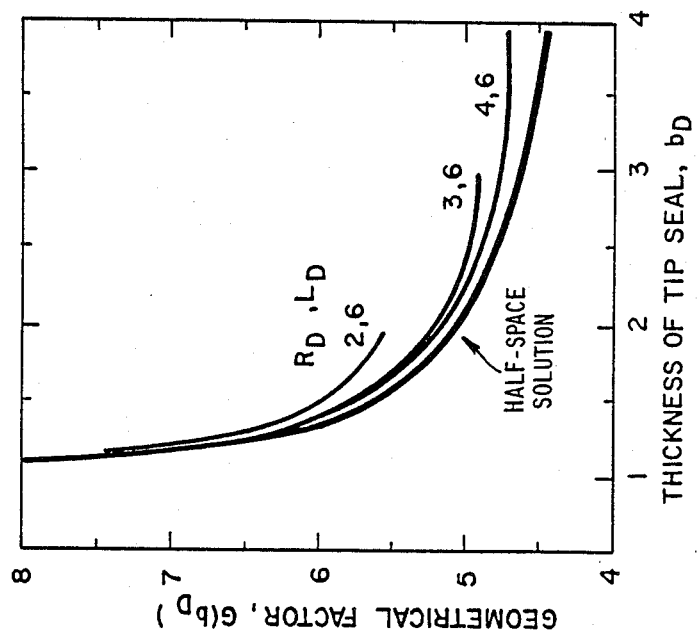
Figure 5:
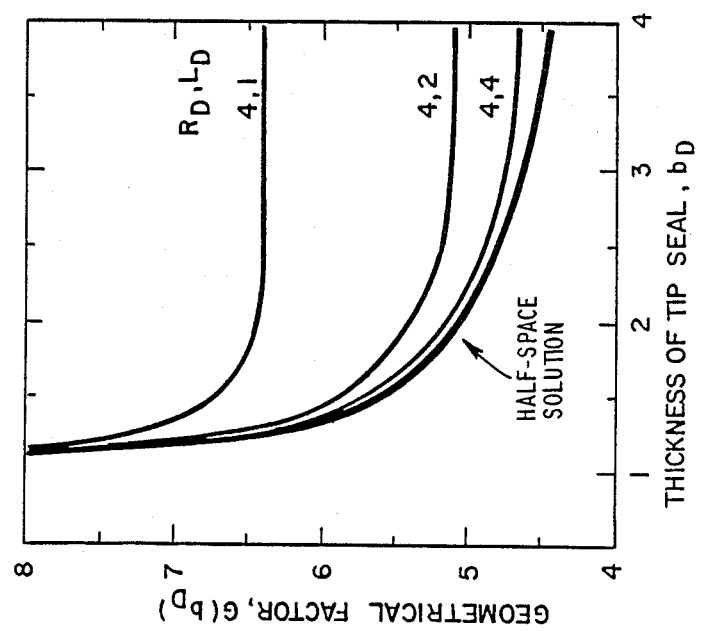

Needless to say, evaluation of the above integral requires numerical procedures. The results of such numerical procedures are shown in FIGS. 4, 5 and 6 which give the value of the geometrical factor for the half-space solution corresponding to an outcrop such as in FIG. 1, and for various values of $R_D$ and $L_D$. The tip 24 as shown in FIG. 1, for example, has an internal radius a of 0.255 cm and an external radius b of 0.485 cm, so that the thickness of the tip seal $b_D$ is 1.9 which has a geometrical factor G of 5.15 for the half-space solution.

It should be noted that the form of Darcy's Law given above may include further refinements or corrections. The viscosity of the gas, for example, can be corrected for temperature effects. For nitrogen, for example, the viscosity in centipoises is given according to
$u_{nitrogen}$=0.018+0.00005 (T-$T_o$)
where $T_0$ is 23° C.

The form of Darcy's Law given above further assumes that the pressure $P_1$ is the pressure at the tip which is not the same as the pressure sensed by the pressure sensors 48 in the instrument box 40. The sensed pressures must be corrected by subtraction of the pressure drop through the airhose 27 which is approximately a linear function of the mass flow rate. This linear function is preferably determined by a calibration procedure which measures the actual pressure drop for various flow rates for unrestricted flow from the injection tip.

The form of Darcy's Law given above is generally valid except at low differential pressures and at high flow rates. At low pressures, the permeability computed from the above equation is greater than the true permeability due to a gas slippage or so-called Klinkenberg effect which is sometimes significant for low permeability samples. Turbulent effects may be significant at high mass flow rates and for a tip having a small internal radius. The mathematical formulae for these corrections are well known in the art since they are applicable to the calculation of permeability when the Hassler-sleeve method is used. These corrections are described in Jones, "A Rapid Accurate Unsteady-State Klinkenberg Permeameter," Society of Petroleum Engineers Journal (October 1972) pages 383–397.

Figure 7:
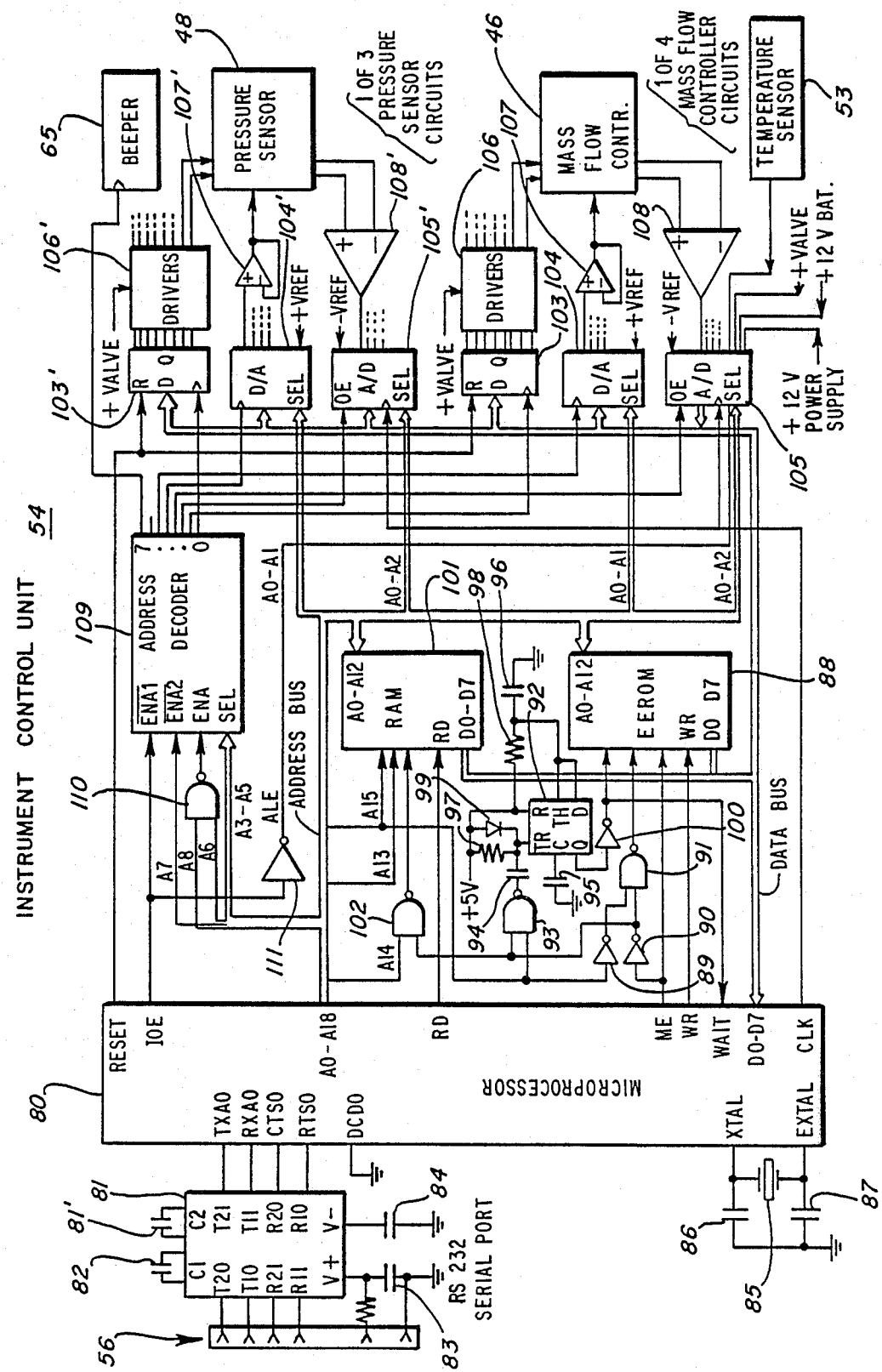
FIG. 7 is a schematic diagram of the instrument control unit in the electronic field permeameter.

Turning now to FIG. 7 there is shown a schematic diagram of the instrument control unit 54. The brains of the control unit are provided by a microprocessor 80, such as part number 64180. The microprocessor 80 is linked to the external microcomputer 23 via an interface circuit 81 such as part number MAX232 which uses four 33 uf capacitors 81', 82, 83 and 84. The microprocessor 80 operates at a 12.2 MHz clocking frequency set by a quartz crystal 85 which works in connection with two 20 pf capacitors 86, 87.

For program storage, the instrument control unit 54 includes 8K bytes of electrically erasable read only memory (EEROM) 88. The EEROM is an integrated circuit such as part number 58064. The EEROM is enabled for addressing by inverters 89, 90 (part number 74HC04) and a NAND gate 91 (part number 74HC00). For programming the EEROM, there is provided a timer 92 (part number 555) which puts the microprocessor into a wait state during the relatively long time required for writing a byte of data into the EEROM. The timer 92 is activated by a NAND gate 93 and works in connection with capacitors 94, 95, and 96, resistors 97, 98, a directional diode 99 and an inverter 100.

For storing data and the results of intermediate computations, the instrument control unit 54 includes 8 K bytes of random access memory 101 provided by an integrated circuit such as part number 6264. A NAND gate 102 in connection with address lines $A_{13}$ and $A_{15}$ enables the RAM 101.

The mass flow controllers 46 are interfaced to the microprocessor 80 via an 8-bit latch 103, a digital-to-analog converter 104, and an analog-to-digital converter 105. The 8-bit latch 103 (part number 74HC273) receives binary signals which turn on the respective electromagnetic valves and mass flow sensors in the mass flow controllers. The logic outputs of the latch 103 are fed to a driver integrated circuit 106, such as part number ULNXXXX.

For setting the mass flow, the outputs of the digital-to-analog converter 104 are buffered by voltage followers 107. The digital-to-analog converter 104 is, for example, part number AD7226, and the voltage followers 107 are part number LM301.

A high impedance differential amplifier circuit 108 buffers the mass flow signal from the mass flow controller 48 before applying it to the analog-to-digital converter 105. The analog-to-digital converter 105 is, for example, part number AD7581. The differential amplifier circuit 108 is described further below in connection with FIG. 9. The analog-to-digital converter 105 also monitors the voltage from the temperature sensor 53, the +VALVE power supply, a 12 volt battery voltage and a 12 volt power supply voltage. These power supply voltages are further shown and described below in connection with FIG. 8.

In FIG. 7 the pressure sensors 48 are shown interfaced to the microprocessor 80 in the same way as the mass flow controllers 46. This is done as a matter of convenience so that the same circuit board can be used for the pressure sensors as is used for the mass flow controllers. The similar components are shown with similar but primed reference numerals. However, it is not necessary to turn the pressure sensors on and off with the latch 103' and drivers 106', and it is not necessary to provide an analog signal to the pressure sensors via the digital-to-analog converter 104' and the followers 107'. Therefore, for used as a permeameter as described above, it is not necessary to wire in the latch 103', the drivers 106', the digital-to-analog converter 104' or the followers 107', although it may be desirable to use these components in a particular application where the additional analog and digital signals could be used.

The microprocessor addresses a particular one of the pressure sensors or mass flow controllers by low order address bits fed to select inputs of the digital-to-analog and analog-to-digital converters, and by addresses fed to an address decoder 109. The address decoder 109 is, for example, part number 74HC138. The address decoder works in connection with a NAND gate 110. In addition to address signals, the analog-to-digital converters receive a clock from the microprocessor 80, and also an address line enable signal provided by an inverter 111. One of the outputs of the address decoder 109 is used to activate the beeper 65. The beeper, for example, includes a one shot which enables an audio oscillator to drive a ceramic piezoelectric transducer.

Figure 8:
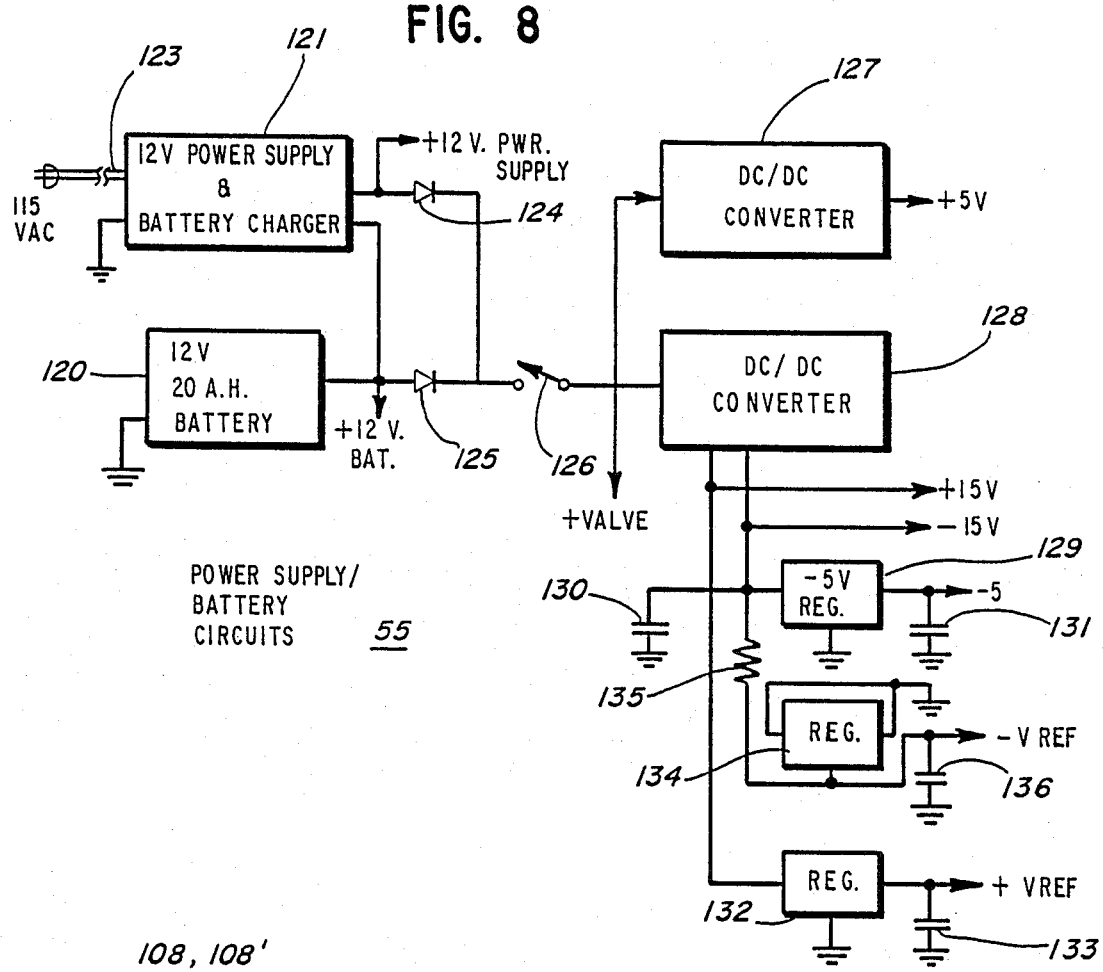
FIG. 8 is a schematic diagram of the power supply for the instrument control unit of the electronic field permeameter.

Turning now to FIG. 8, there is shown a schematic diagram of the power supply circuits. For field use the electronic field permeameter is powered by a 12 volt, 20 ampere hour storage battery 120. For charging the battery and for operation in the laboratory, the permeameter also includes a conventional 12 volt power supply and batter charger 121 which receives 115 VAC line power from an extension cord received in a socket 123. A pair of directional diodes 124, 125 permit the battery to be charged and the permeameter to be operated at the same time. Moreover, the diodes 124, 125 permit independent power supply and battery voltages to be generated. Since these separate voltages are fed to separate inputs of the analog-to-digital converter 105 of FIG. 7, it is possible for the microprocessor 80 to automatically determine whether the permeameter is being powered by the power supply or the battery, and to monitor the charging of the battery while the permeameter is operated.

A switch 126 is provided to turn the permeameter on and off. The unregulated power at about 11 volts is used for the +VALVE supply, and is also used to power a first DC/DC converter 127 providing a +5 volt supply to the logic circuits, and a second DC/DC converter 128 providing a +15 volt and a −15 volt supply for the amplifiers. The first DC/DC converter is a part number 50DIGITAL51. The second DC/DC converter is a part number 50ANALOG51. The −15 volt supply is fed to a −5 volt regulator 129 to provide a −5 volt supply to the digital-to-analog converters. The −5 volt regulator is, for example, part number NEG5VA. The regulator 128 has 2.2 uF input and output capacitors 130, 131. The digital-to-analog converters (104, 104' in FIG. 7 also use a +VREF voltage provided by a precision regulator 132 which uses a 0.1 uF output capacitor 133. The analog-to-digital converters (105, 105' in FIG. 7) use a −VREF supply which is provided by a precision regulator 134 which operates as a shunt regulator in connection with a 122 ohm series resistor 135 and a 0.1 uF output capacitor 136. The precision regulators are, for example, part number AD581.

Figure 9:
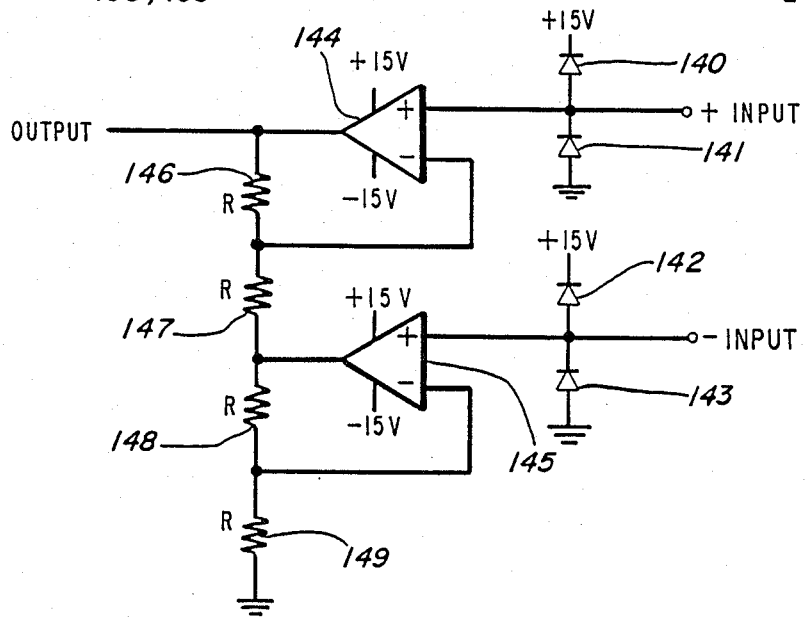
FIG. 9 is a schematic diagram of one of the differential amplifiers used in the electronic field permeameter.

Turning now to FIG. 9, there is shown a schematic diagram of the differential amplifiers 108, 108' used for buffering the pressure sensor and mass flow signals fed to the analog-to-digital converters. For transient protection the positive and negative inputs are clamped to between ground and +15 V supply by directional diodes 140, 141, 142 and 143. To provide a high input impedance, both the positive input and the negative input of the differential amplifier are fed to the positive inputs of respective operational amplifiers 144, 145. The operational amplifiers are, for example, part number TL064. The outputs and negative inputs of the two operational amplifiers are fed to a precision voltage divider including four matched resistors 146, 147, 148 and 149. Due to the negative feedback to the operational amplifiers, the output of the circuit in FIG. 9 is twice the voltage difference between its inputs.

Figure 10:
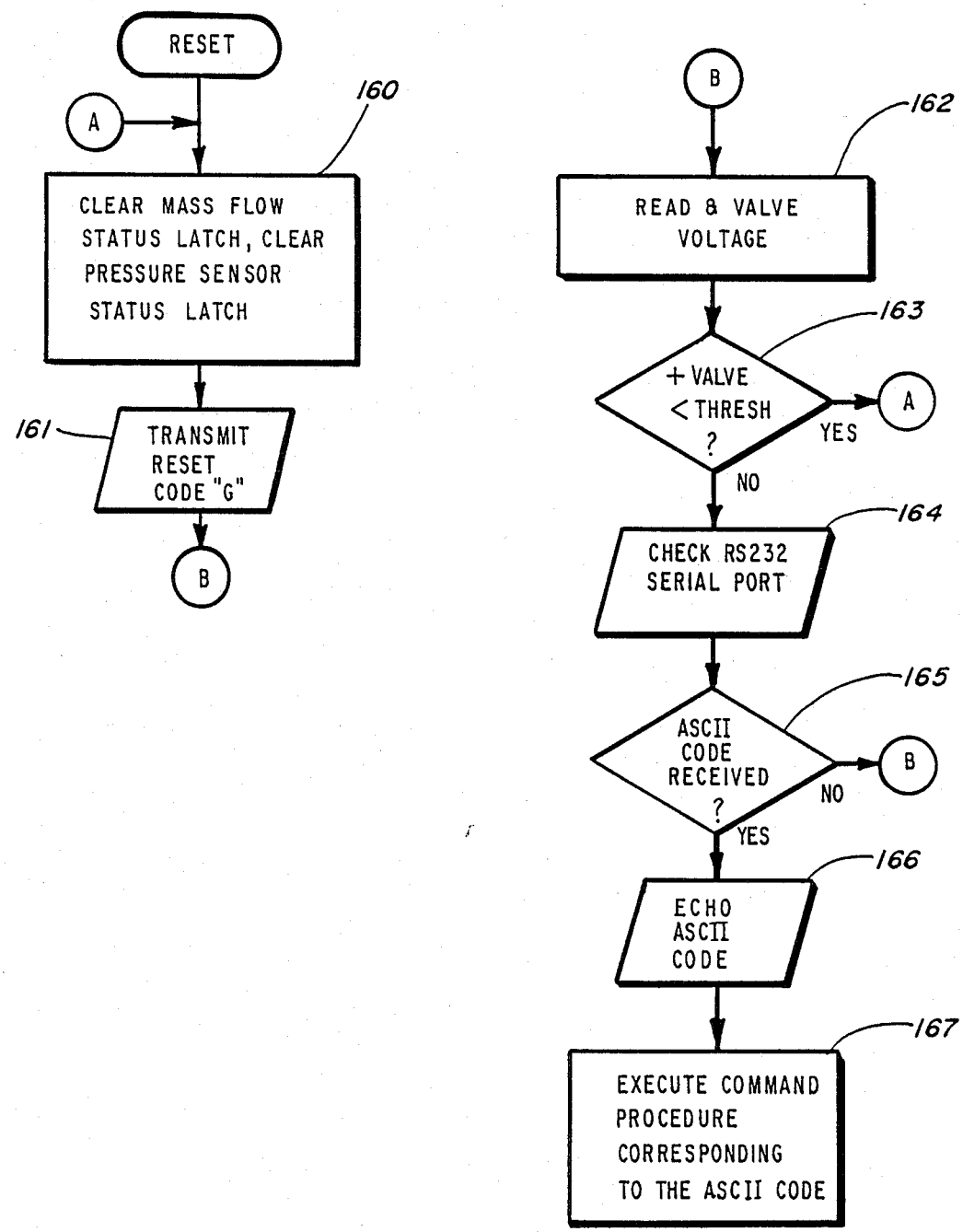
FIG. 10 is a flowchart of the control procedure executed by the instrument control unit.

Turning now to FIG. 10, there is shown a flowchart of a procedure for execution by the microprocessor 80 of FIG. 7 in order to receive the command codes of FIG. 3. The procedure is executed when the microprocessor becomes reset when power is switched on to the permeameter. In the first step 160 the latches 103 and 103, determining the status of the mass flow controllers and the pressure sensors, are cleared. This insures that the pressure sensors and mass flow controllers are shut off. In order to tell the external microcomputer that a reset has occurred, in step 161 the reset code "G" is transmitted from the microprocessor to the external microcomputer. Next, in step 162, the permeameter s power supply is checked by reading the +VALVE voltage from the analog-to-digital converter 105 (see FIG. 7). If this voltage is less than a predetermined threshold such as 10 volts, then in step 163 execution jumps back to step 160 to turn off the mass flow controllers and pressure sensors. This insures that they are not operated with an excessively low power supply voltage.

If the power supply voltage is less than the threshold voltage, then in step 164 the RS232 serial port is checked for any incoming ASCII characters. If an ASCII character is not received, then execution jumps back in step 162 to continuously monitor the power supply voltage. Once an ASCII code is received, then in step 166 receipt of the code is acknowledged by echoing the code back to the external microcomputer. Finally, in step 167 the command procedure corresponding to the ASCII code is executed.

Figure 11:
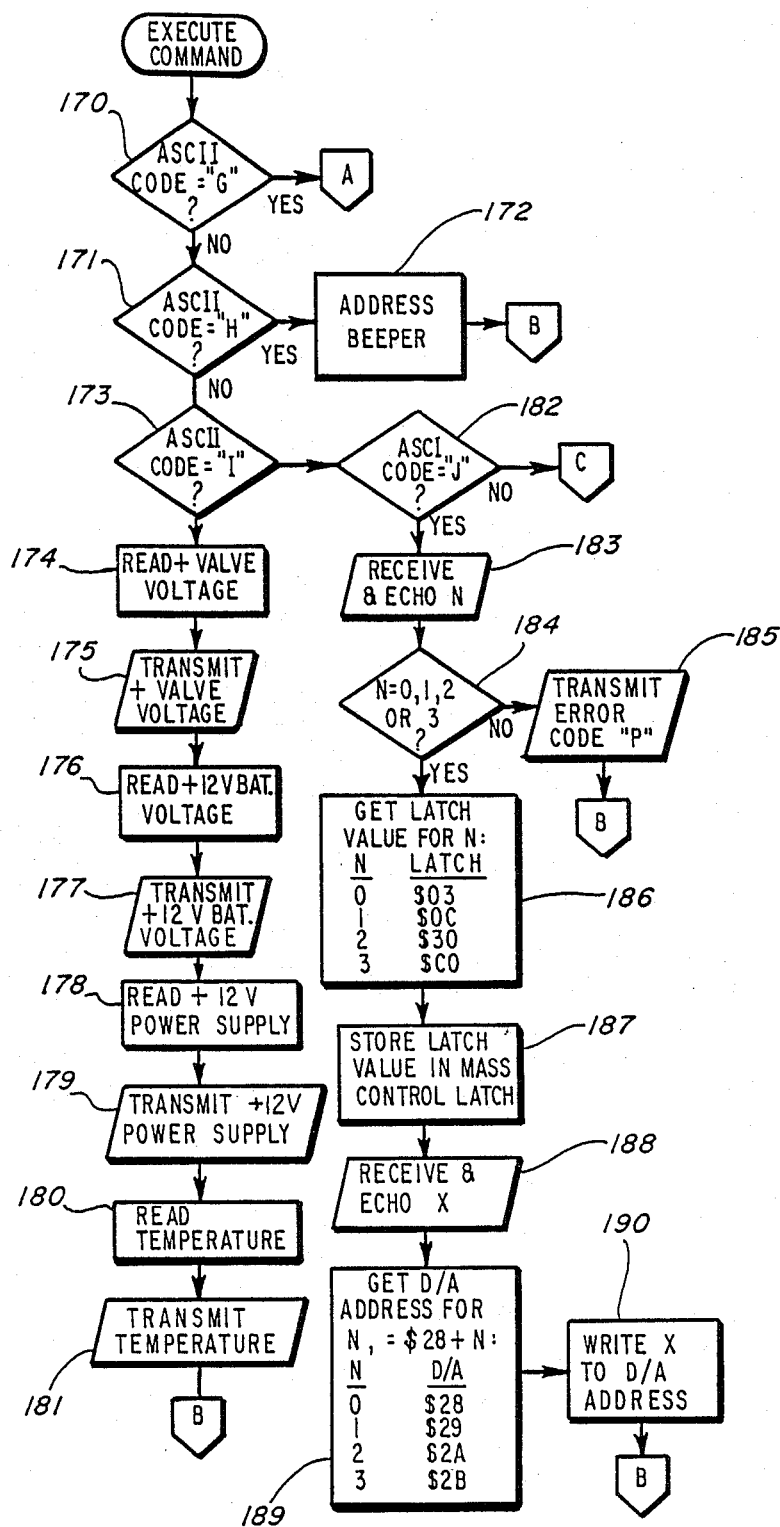
FIGS. 11, 12 and 13 comprise a flowchart of a procedure used by the instrument control unit for executing a control command.

Turning now to FIG. 11, there is shown the procedure for recognizing and executing the ASCII code characters. In step 170, execution jumps back to step 160 if the ASCII code is a "G" reset code. In step 171, if the ASCII code is found to be an "H", then in step 172 the beeper is addressed and execution continues in step 162. Otherwise, execution branches to step 173 to test whether the ASCII code is "I" If so, then the status of the permeameter instruments is checked in step 174 by reading the +VALVE voltage, and in step 175 transmitting the voltage value over the serial link to the external microcomputer. In step 176, the analog-to-digital converter (105 in FIG. 7) reads the battery voltage and in step 177 the value of the battery voltage is transmitted to the external microcomputer. In step 178 the analog-to-digital converter reads the +12 volt power supply voltage, and in step 179 the value of the power supply voltage is transmitted to the external microcomputer. In step 180, the analog-to-digital converter reads the temperature from the temperature sensor 53, and in step 181 the value of the temperature is transmitted to the external microcomputer. Execution is then continued in step 162 of FIG. 10.

If in step 173 it was found that the ASCII code was not a "I", then in step 182 the microprocessor checks whether the ASCII code is a "J". If it is, then in step 183 the value of a parameter N is received from the external microcomputer and echoed. If the value of N is neither 0, 1, 2 or 3, then in step 184 execution branches to step 185 to transmit an error code "P" back to the external microcomputer. Otherwise, in step 186, a particular value is obtained depending on the value of N. This value is the value to be transmitted to the latch 103 which determines which of the mass flow controllers are energized. In step 187 the latch value is stored in the latch. Next, in step 188 the value of the parameter "X" is received and echoed. This parameter is the set point for the selected mass flow controller. In step 189 the address for the digital-to-analog converter is obtained for sending the set point to the selected mass flow controller. Finally, in step 190, the value of the set point is written to the previously determined digital-to-analog converter address. Execution continues back in step 162 of FIG. 10.

Figure 12:
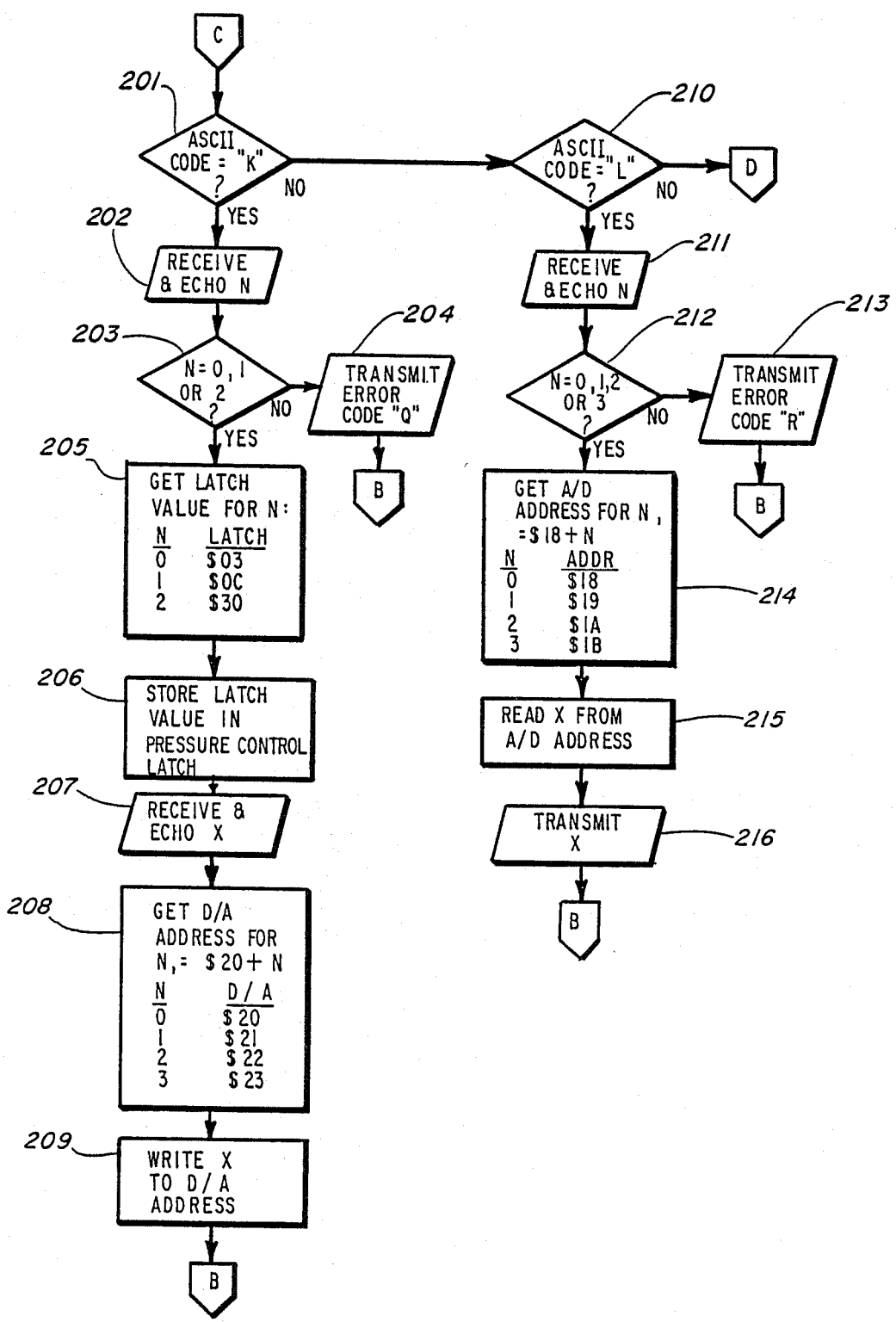

If in step 182 the ASCII code was not found to be a "J", then execution continues in FIG. 12. In step 201 execution branches to step 202 if the ASCII code is a "K". If so, the external microcomputer is requesting that a selected one of the pressure sensors should be turned on. For this purpose in step 202 the parameter N is received and echoed. The parameter N specifies which of the pressure sensors are to be turned on. In step 203 execution branches if N is neither a 0, 1 or 2. In this case, in sep 204 an error code "Q" is transmitted back to the external microcomputer, and execution continues back in step 162 of FIG. 10. Otherwise, in step 205 a latch value is obtained depending on the value of N. Then in step 206 the value so obtained is stored in the latch 103, controlling the pressure sensors (see FIG. 7). Next in step 207, the value of the set-point parameter X is received from the external microcomputer and echoed. In step 208 the digital-to-analog converter address for the selected pressure sensor is obtained as a function of the value of N. Finally, in step 209 the value of the set-point parameter X is written to the digital-to-analog converter address obtained in step 208. Execution continues back in step 162 of FIG. 10.

If in step 201 the ASCII code was not found to be a "K", then in step 210 the ASCII code is compared to an "L" If the ASCII code is an "L", then the external microcomputer is requesting the value of the mass flow from a selected one of the mass flow controllers. In step 211 the value of the parameter N is received and echoed. Next in step 212, execution branches if N is neither a 0, 1, 2 or 3. If so, then in step 213 an error code "R" is transmitted back to the external microcomputer, and execution jumps back to step 162 of FIG. 10. Otherwise, in step 214, the analog-to-digital converter address corresponding to the selected mass flow controller is obtained. In step 215 the value of the mass flow is read from the analog-to-digital converter address obtained in step 214. In step 216 the value of the mass flow is transmitted to the external microcomputer. Execution continues back in step 162 of FIG. 10.

Figure 13:
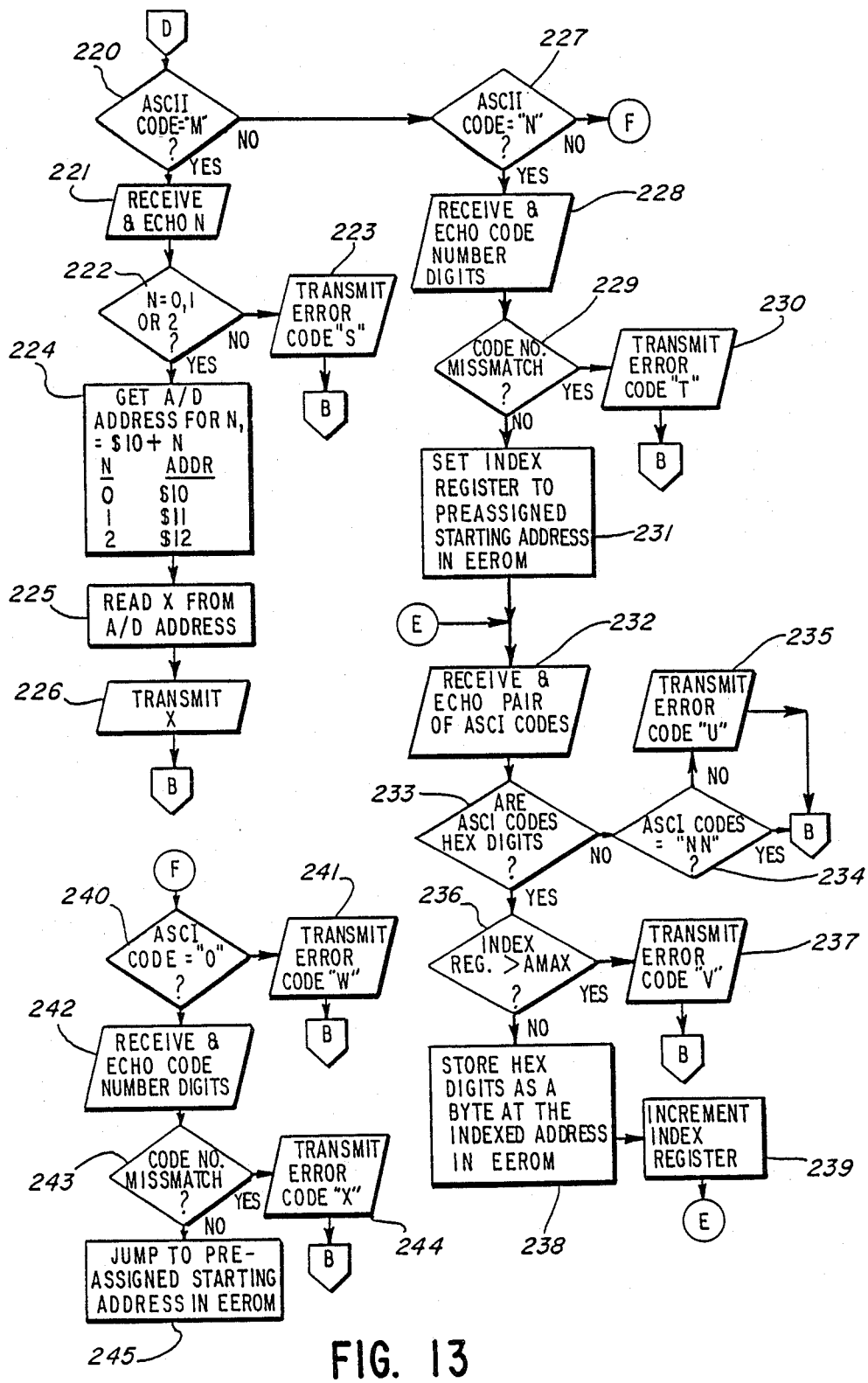

If in step 210 the ASCII code was found to be something different from "L", then execution continues in FIG. 13. In step 220 the ASCII code is compared to an "M". If it is found to be an "M", then the external microcomputer is requesting the pressure value from a selected pressure sensor. To select the pressure sensor, in step 221 the value of the parameter N is received and echoed. In step 222 execution branches if the value of N is neither a 0, 1 or 2. In this case, in step 223 an error code "S" is transmitted to the external microcomputer and execution continues in step 162 of FIG. 10. Otherwise, in step 224 the analog-to-digital converter address for the selected pressure sensor is obtained. In step 225 the value of the pressure is read from the analog-to-digital converter address obtained in step 224. Finally, in step 226 the pressure value is transmitted to the external microcomputer and execution continues in step 162 of FIG. 10.

If in step 220 the ASCII code was found to be something different from an "M", then in step 227 the code is compared to an "N". If the ASCII code is found to be an "N", then the external microcomputer is requesting that a custom program be loaded into the EEROM. For this purpose in step 228 the digits of the code number are received and echoed. In step 229 the received digits are compared to a prestored version of the code number, and if the digits received from the external microcomputer do not match the digits of the prestored code number, then in step 230 an error code is transmitted to the external microcomputer, and execution continues back in step 162 of FIG. 10. Otherwise, in step 231 an index register is set to a preassigned starting address in EEROM. In order to prevent the program currently being executed by the microprocessor from being reprogrammed, a portion of the EEROM different from the currently executed program is set aside to receive the custom program, starting with this preassigned starting address. Then, in step 232 pairs of ASCII codes representing hexadecimal digits making up program bytes are received and echoed. Next in step 233 the ASCII codes are checked to make sure that they represent hexadecimal digits. If not, then the pair of codes could represent the termination code for the custom program. This termination code consists of "NN". In step 234 the loading of the program is completed if the pair of ASCII codes are "NN" Otherwise, in step 235 an error code "U" is transmitted and execution continues back in step 162 of FIG. 10.

If in step 233 it is found that the pair of ASCII codes represent hexadecimal digits, then in step 236 the index register is compared to a predetermined number AMAX to determine whether all of the available EEROM space has been reprogrammed. If so, then the programming process is terminated and in step 237 an error code "V" is transmitted and execution continues back in step 162 of FIG. 10. Otherwise, in step 238 the pair of ASCII codes representing hexadecimal digits are stored as a byte at the indexed address in EEROM. In step 239 the index register is incremented and execution jumps back to step 232 to receive the next pair of ASCII codes for the custom program.

If in step 227 it was found that the ASCII code was not an "N", then in step 240 the code is compared to an "O". If the ASCII code is not an "O", then something other than a command code in the table 70 of FIG. 3 was transmitted. To indicate this fact, an error code "W" is transmitted in step 241, and execution continues back in step 162 of FIG. 10.

If an ASCII code "O" is received, then the external microcomputer is requesting the execution of a custom program. In this case in step 242 the hexadecimal digits of the code number are received and echoed. In step 243 the received code digits are compared to prestored code digits, and if a mismatch occurs an error code "X" is transmitted in step 244, and execution continues back in step 162 of FIG. 10. Otherwise, if the transmitted code number matches the prestored code number, then in step 245 execution jumps to the preassigned starting address of the custom program in EEROM. This completes the description of the procedure executed by the microprocessor 80 in the instrument box.

Figure 14:
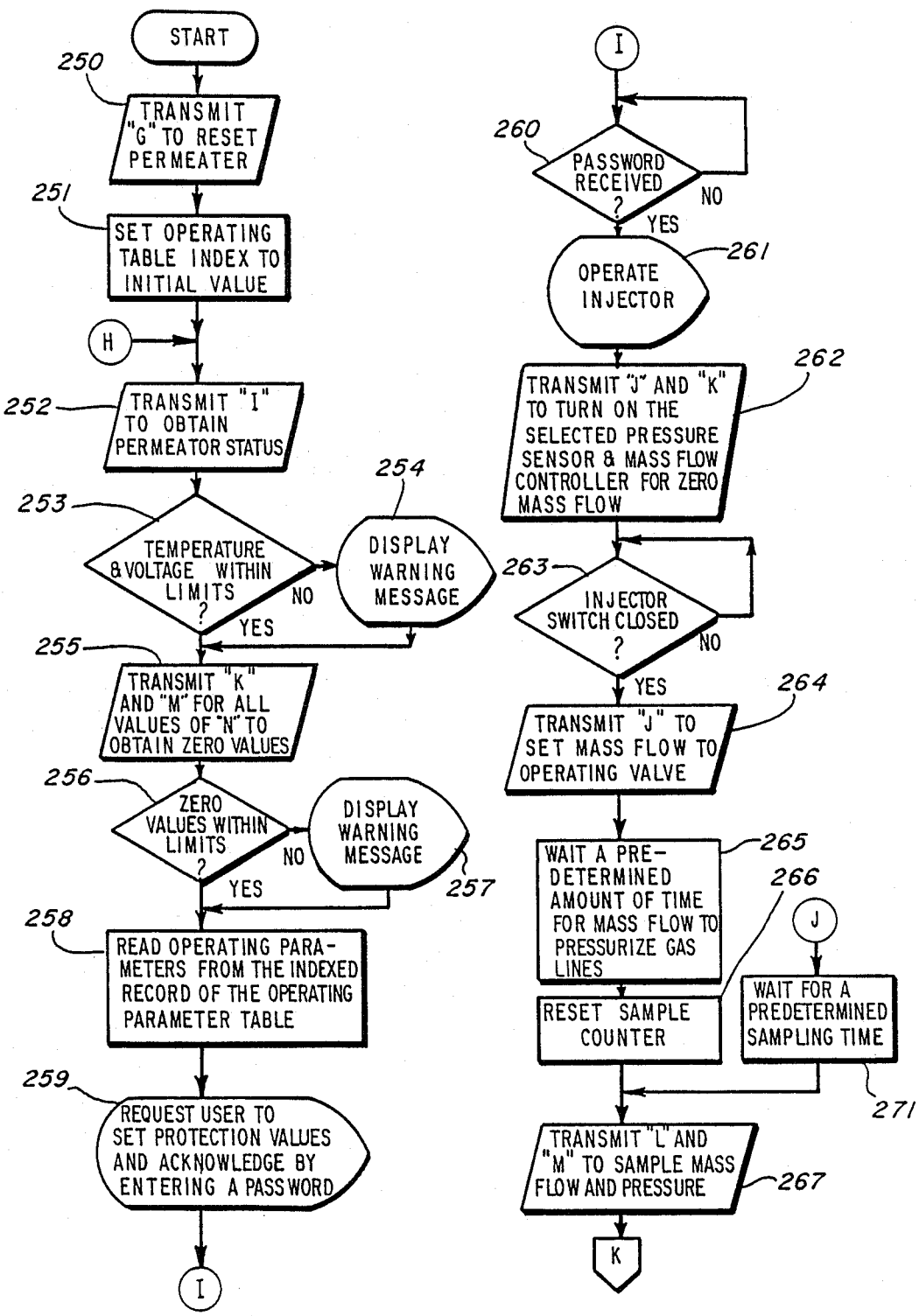
FIGS. 14 and 15 comprise a flowchart of a control procedure executed by a supervisory microcomputer in order to measure rock permeability by operating the instrument control unit.

Turning now to FIG. 14 there is shown a flowchart of the basic procedure executed by the external microcomputer 23 for taking a permeability measurement. In the first step 250, a "G" command is transmitted to the instrument box in order to reset the permeameter. Then, in step 251 an operating table index is set to an initial value. It should be apparent that in order to take a permeability measurement, a mass flow sensor must be selected along with a mass flow set point, and also a pressure sensor must be selected. The microcomputer has prestored in its memory a table of typical operating parameters. Unless the user specifies otherwise, a conservative set of operating parameters are first selected by the microcomputer. The initial selection, for example, includes a mid-range mass flow rate of 300 sscm and the maximum pressure range of 0–200 psid. In step 251 the index of the record in the operating table including these conservative parameters is selected.

Next, in step 252, an "I" command is transmitted to obtain the status of the permeameter. In step 253 the temperature and voltages are compared to predefined limits and if they are outside of these predefined limits, a warning message is displayed in step 254. Then, in step 255, a "K" and an "M" command are transmitted for all of the values of "N" in order to obtain zero values for the pressures sensed by the pressure sensors. In step 256 the zero values are compared to predefined limits, and if they are found to be outside of the limits, an error message is displayed in step 257.

Now that the operating status of the permeameter has been checked, in step 258 the operating parameters are read from the indexed record of the operating parameter table. Depending on these operating parameters, in step 259 a request is displayed to the user to set the protection valves to the required positions, and further to request that the user enter a password to acknowledge that the valves have been properly set. In step 260 operation of the permeameter is prohibited until a correct password is received. Once the password has been received, a message is displayed in step 261 telling the user to operate the injector. Next, in step 262, a "J" command and a "K" command are transmitted so that the selected pressure sensor and mass flow controller are turned on, but the mass flow set point is at this time set to zero in order to conserve the gas supply.

In step 263 the microcomputer waits until the user closes the injector switch (64 in FIG. 1), and once the injector switch is closed, in step 264 a J" command is transmitted to set the mass flow to the operating value. In step 265, the microcomputer waits a predetermined amount of time for the mass flow to pressurize the gas lines. Soon after this time, a steady-state condition might be achieved. For detecting this steady-state condition, a sample counter is reset in step 266. In step 267, an "L" code and an "M" code are transmitted in order to obtain a mass flow value and a pressure value.

Figure 15:
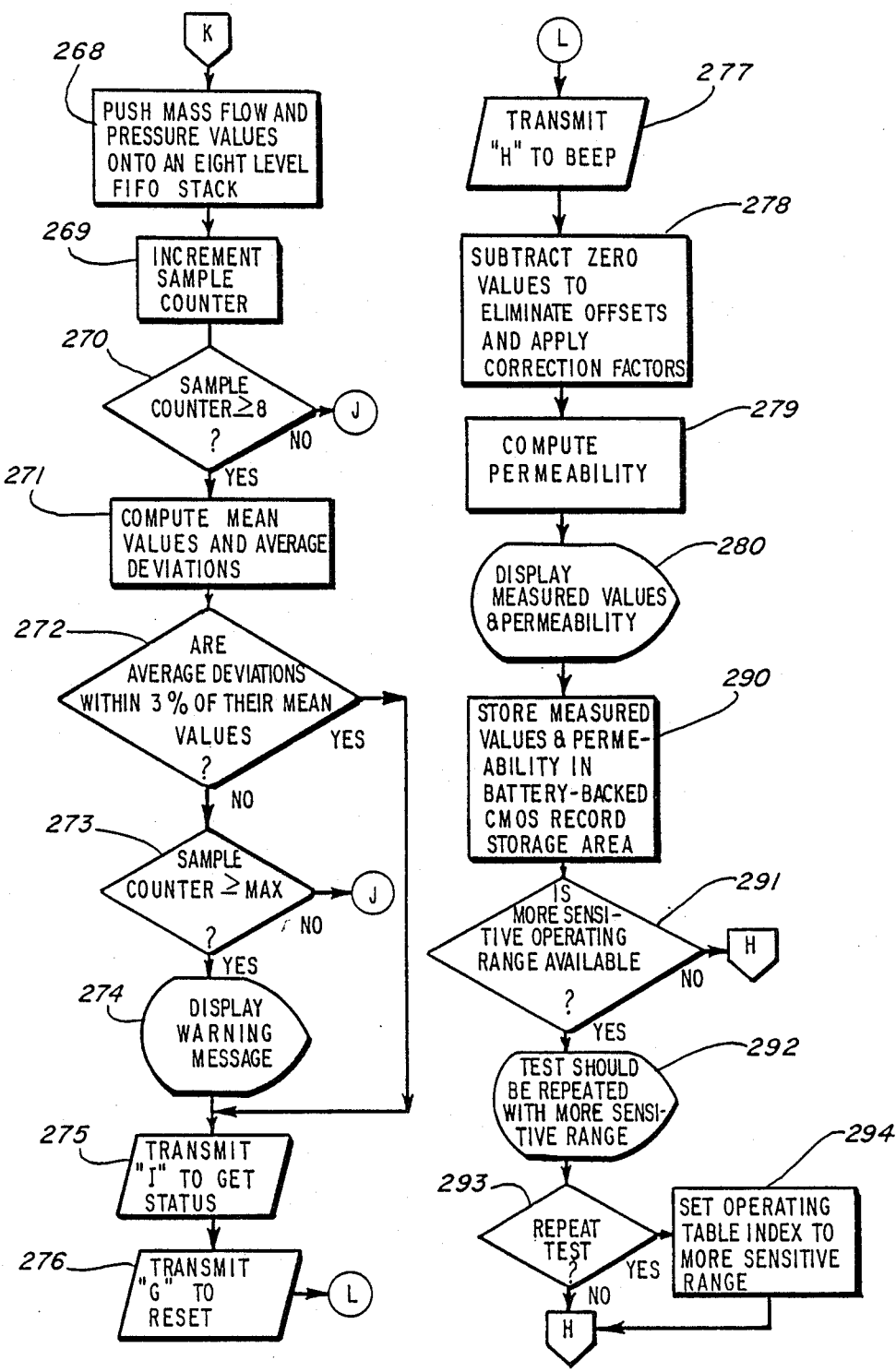

Execution continues in FIG. 15. In step 268, the mass flow and pressure values are pushed onto an eight level first-in-first-out stack. Then, in step 269 the sample counter is incremented and in step 270 the sample counter is compared to eight to determine whether the stack is full. If not, execution jumps to step to 271 in FIG. 14, whereupon the microcomputer waits a predetermined sampling time before obtaining additional samples. The sample time is preferably about 50 milliseconds in order to obtain a 20 Hz sampling rate.

Returning to FIG. 15, once the stack is full, then in step 271 the mean values and average deviations of the respective mass flow and pressure values in the stack are computed. For determining whether a steady-state has been reached, in step 272 the average deviations are compared to three percent of their respective mean values. If average deviations are not within three percent of their respective mean values, then sampling continues unless the sample counter exceeds a predetermined large number MAX. As tested in step 273, if this predetermined large number is not exceeded, execution jumps back to step 271 of FIG. 14 to continue the sampling process. Otherwise, a warning message is displayed to the operator in step 274 and execution continues on the assumption that the gas flow has reached the most steady-state possible.

Once steady-state has been reached, in step 275 the external microcomputer transmits an "I" command to obtain the status of the permeameter, and finally the sampling process is finished in step 276 by transmitting a "G" command to reset the permeameter and thereby shut off the gas flow.

To tell the operator that the sampling process has been completed, in step 277 an "H" command is transmitted to activate the beeper. In step 278 the zero values are subtracted from the measured values to eliminate offsets, and correction factors are applied, for example, to correct for the pressure drop along the flexible hose 27 (see FIG. 1), and to correct for the temperature dependence of the gas viscosity. Then, in step 279, the permeability of the test sample is computed by applying the known procedures for computing permeability. These known procedures are shown in Appendix I. In step 280 the computed permeability is displayed along with the measured values and conditions upon which the computed permeability was based. Next, in step 290 the measured values and the computed permeability is stored in a record storage area of the battery-backed CMOS RAM (62 in FIG. 2). Therefore, this data will be available to transfer to a central data processing facility, even after the power to the microcomputer is shut off.

Since the initial operating parameters were very conservative, it is possible that more sensitive operating ranges are available for determining the permeability of the current test sample. In step 291 the measured pressure or the permeability is compared to limits prestored in the operating table to determine whether a more sensitive range is available. If not, execution jumps back to step 252 in order to continue the permeability measurement using the same operating ranges. Otherwise, in step 292 the operator is told that a more sensitive range is available and the operator is given the option of repeating the current test with the more sensitive range. If in step 293 the user wants the current test repeated, then in step 294 the operating table index is set to point to the more sensitive operating range, and execution jumps back to step 252 to repeat the test using the more sensitive range of operating parameters.

In the flowchart of FIGS. 14 and 15, the most basic procedure for operating the permeameter has been described. It should be noted, however, that for more specific applications and unusual conditions it is preferable to allow the user to deviate from the basic procedure, and to change the operating parameters. It is also desirable to program the microcomputer 23 to assist the user in using the permeameter, to permit the user to correlate the test results with other information about the test samples or the test environment, and to give the user extensive control over the recording of data.

Figure 16:
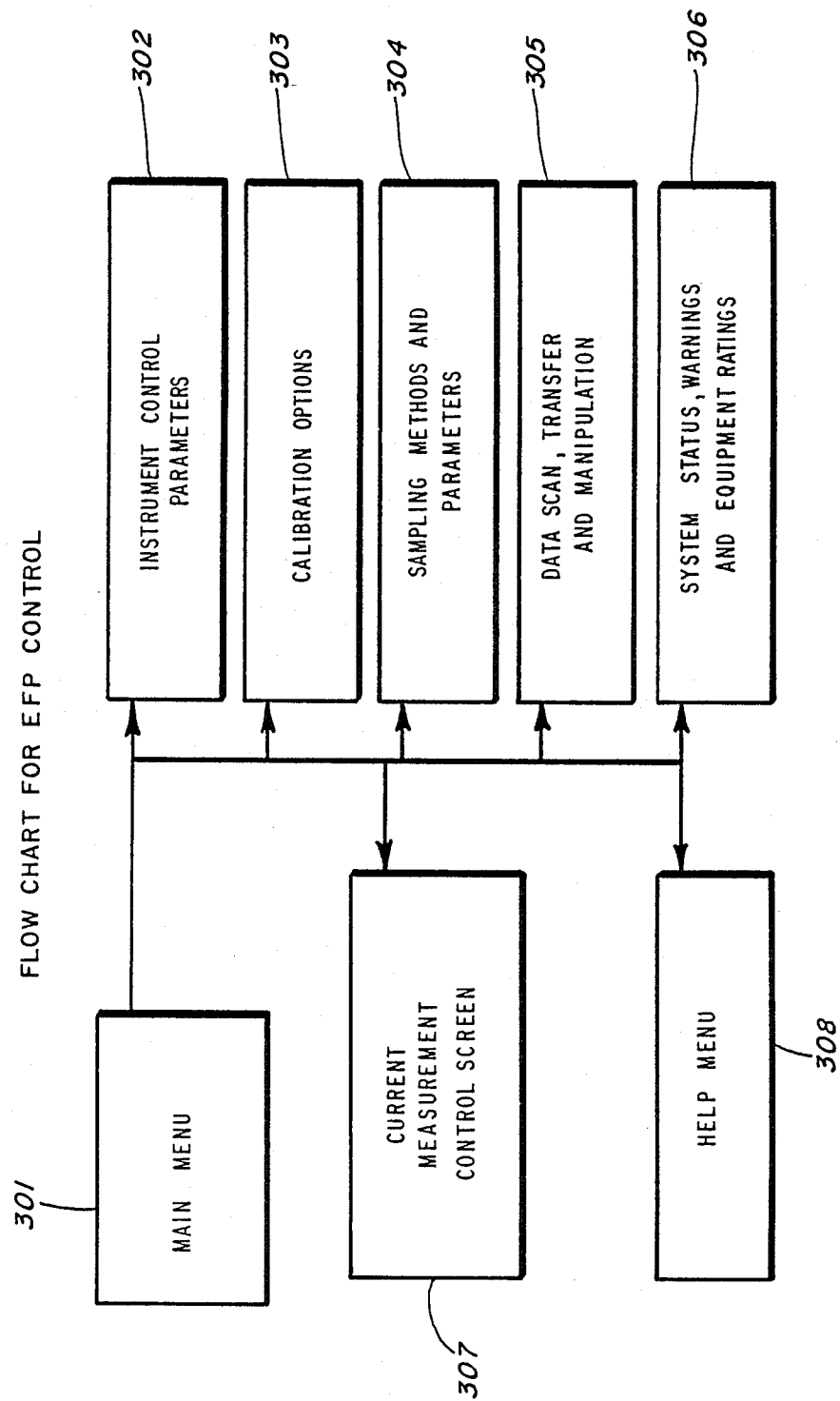
FIG. 16 is a flowchart of an executive procedure executed by the supervisory computer for interacting with the user as further shown in the screen displays of Appendix II.

Turning now to FIG. 16, there is shown a top-level flowchart of various options that a user may desire for operating the electronic field permeameter of the present invention. When the external microcomputer is first turned on, for example, in step 301 a main menu is displayed. This main menu appears in Appendix II, along with other display screens corresponding to the steps in the flowchart of FIG. 16. Depending upon the user response to the main menu, the executive program branches to a subprocedure including a procedure 302 for inspecting or adjusting instrument control parameters, a procedure 303 for calibrating the permeameter, a procedure 304 for selecting sampling methods and adjusting sampling parameters, a procedure 305 for data scan, transfer and manipulation, a procedure 306 for reviewing the system status, warnings, and equipment ratings, and a procedure 307 for performing a measurement in accordance with the basic procedure described above. If the user does not understand how to use any of these procedures, there is also provided a procedure 308 for displaying a help menu allowing the user to ask questions about how to use the available procedures.

It should be evident from the screen displays in Appendix II that the menus give a wide range of options yet also prevent the user from making inconsistent selections of operating parameters. Another feature illustrated by the screen displays in Appendix II is the provision of an "electronic notebook" for recording the location and specific geological features associated with each measurement.

In view of the above, there has been described a field permeameter that automatically controls the flow of gas to an injection tip, determines when steady-state conditions have been obtained, automatically senses and records the steady-state mass flow and pressure, automatically shuts off the gas supply as soon as possible, emits an audio signal telling the user that the measurement has been completed, and computes the permeability. Therefore, the field permeameter is capable of very rapid operation and conserves the supply of pressurized gas. Moreover, the mass flow controllers and the pressure sensors are more precise than rotameters and mechanical gauges, and are insensitive to the orientation or leveling of the instrument box. Since the recording of data is automatic and error messages are displayed for any inconsistent or unusual operating conditions, operator errors are virtually eliminated. Moreover, the components of the permeameter are readily transported and assembled in the field. The components are especially compact, lightweight and durable for use at remote field sites.

The electronic field permeameter of the present invention is especially useful for measuring in situ permeabilities of outcrop rock in order to study rock properties and determine spatial distribution of fluid flow heterogeneities. Small or large-scale anisotropies can be measured in the outcrop. Homogeneous or heterogeneous rock samples can be selected for further laboratory experiments. In the laboratory, the small or large-scale anisotropies can be measured on hand samples, which is particularly useful for small-scale analysis of variabilities. Also, detailed permeability surveys of slabbed cores can be conducted in the laboratory. Moreover, by making appropriate connections to the vent and outlet of the instrument box, permeability can be measured at high inlet and outlet pressures, and porosity can be measured via transient analysis.

Since the injection tips are readily interchangeable, various kinds of tips can be used for receiving small core plugs or unconsolidated sands. Also, multiple tip arrangements in linear or rectangular arrays could be used for automatic, synchronous measurements of permeability.

APPENDIX I

COMPUTER PROGRAM FOR COMPUTING PERMEABILITY

```
      PROGRAM BKCALC(INPUT,TAPE5=INPUT,OUTPUT,TAPE6=OUTPUT,
     &                KOUT,TAPE7=KOUT)
C
C     **********************************************************
C
C     VARIABLE DEFINITION:
C
C         ITYPE:    1 = CONVENTIONAL 1-D CORE PLUG MEASUREMENT
C                   2 = FIELD PERMEAMETER MEASUREMENT
C
```

```
C      IMODE:    1 = FLOW RATE IN XFS FROM ROTAMETERS
C                2 = FLOW RATE IN CC/SEC FROM ROTAMETERS
C                3 = FLOW RATE IN STANDARD CC/SEC FROM BUBBLE METER
C
C      IMETH:    1 :  X = 2(VIS)(LENGTH)/(FLUX)      (CP-SEC)
C                     Y = DELP**2/(FLUX**2)          (ATM-SEC/CM)**2
C
C                2 :  X = (FLUX)(LENGTH)             (CM**2/SEC)
C                     Y = DELP**2/(FLUX)             (ATM**2-SEC/CM)
C
C                3 :  X = (FLUX)/(ARAD*GEOM)         (1/SEC)
C                     Y = DELP**2/(FLOW RATE)        (ATM**2-SEC/CM**3)
C
C      ***************************************************************
C
C
       DIMENSION RMETER(10),ILABEL(5)
       REAL TTLPERM, AVGPERM
C
C
       RMETER(1)=471.94744
       RMETER(2)=165.18161
       RMETER(3)=55.060535
       RMETER(4)=100.*21.237635/2.7
       RMETER(5)=8.6523698
       RMETER(6)=130./60.
       RMETER(7)=50./60.
C
C
       PI = 2.*ACOS(0.)
       VIS = 0.018
       AVGPERM = 0.0
       TTLPERM = 0.0
C
       READ(5,*) NSETS,ITYPE
       DO 500 I=1,NSETS
C
C
       IF(ITYPE.EQ.2) GO TO 10
       READ(5,5000) (ILABEL(J),J=1,5)
       READ(5,*) NDATA,CORED,COREL,IMODE,IMETH
       CORER=CORED/2.
       AREA=PI*CORER**2
       WRITE(6,1000) (ILABEL(J),J=1,5),NDATA,CORED,COREL,AREA,
     &               IMODE,IMETH
       IF(IMODE.GT.1) GO TO 300
       GO TO 100
C
C
  10   READ(5,5000) (ILABEL(J),J=1,5)
       READ(5,*) NDATA,ARAD,GEOM,IMODE,IMETH
       AREA=PI*ARAD**2
       WRITE(6,1100) (ILABEL(J),J=1,5),NDATA,ARAD,GEOM,AREA,
     &               IMODE,IMETH
       IF(IMODE.GT.1) GO TO 300
C
C
 100   IF(IMETH.EQ.1) WRITE(6,2000)
       IF(IMETH.EQ.2) WRITE(6,2100)
       IF(IMETH.EQ.3) WRITE(6,2200)
       IF(IMETH.EQ.4) WRITE(6,2300)
C
       DO 200 J=1,NDATA
          READ(5,*) IMETER,FRM,DP
          DPA=(DP+14.696)/14.696
          FR=FRM*DPA*RMETER(IMETER)/100.
```

```
          IF(IMETER.EQ.6) FR=DPA*(0.01121*FRM-0.08)
          DELP=DPA**2 - 1.
          PINV=2./(1.+DPA)
          U=FR/AREA
C
          IF(ITYPE.EQ.1) PERMA=(FR*VIS*COREL*2000.)/(AREA*DELP)
          IF(ITYPE.EQ.2) PERMA=(FR*VIS*2000.)/(ARAD*GEOM*DELP)
C
          WRITE(7,9000) PERMA
C
          IF(IMETH.EQ.4) GO TO 180
          IF(IMETH.EQ.3) GO TO 170
          IF(IMETH.EQ.2) GO TO 160
C
          XCOORD=2.*VIS*COREL/U
          YCOORD=DELP/U**2
          GO TO 190
C
  160     XCOORD=U*COREL
          YCOORD=DELP/U
          GO TO 190
C
  170     XCOORD=U/(ARAD*GEOM*4.14073E8)
          YCOORD=DELP/FR
          GO TO 190
C
  180     CONTINUE
  190     WRITE(6,4000) J,IMETER,FRM,DP,PINV,PERMA,XCOORD,YCOORD
C
          TTLPERM = PERMA + TTLPERM
C
C
  200     CONTINUE
          GO TO 500
C
C
C
  300     IF(IMETH.EQ.1) WRITE(6,3000)
          IF(IMETH.EQ.2) WRITE(6,3100)
          IF(IMETH.EQ.3) WRITE(6,3200)
          IF(IMETH.EQ.4) WRITE(6,3300)
C
          DO 400 J=1,NDATA
            READ(5,*) FR,DP
            DPA=(DP+14.696)/14.696
            IF(IMODE.EQ.2) FR=FR*DPA
            DELP=DPA**2-1.
            PINV=2./(1.+DPA)
            U=FR/AREA
C
          IF(ITYPE.EQ.1) PERMA=(FR*VIS*COREL*2000.)/(AREA*DELP)
          IF(ITYPE.EQ.2) PERMA=(FR*VIS*2000.)/(ARAD*GEOM*DELP)
C
          WRITE(7,9000) PERMA
C
          IF(IMETH.EQ.4) GO TO 380
          IF(IMETH.EQ.3) GO TO 370
          IF(IMETH.EQ.2) GO TO 360
C
          XCOORD=2.*VIS*COREL/U
          YCOORD=DELP/U**2
          GO TO 390
C
```

```
  360     XCOORD=U*COREL
          YCOORD=DELP/U
          GO TO 390
C
  370     XCOORD=U/(ARAD*GEOM*4.14073E8)
          YCOORD=DELP/FR
          GO TO 390
C
  380     CONTINUE
  390     WRITE(6,4500) J,FR,DP,PINV,PERMA,XCOORD,YCOORD
C
          TTLPERM = PERMA + TTLPERM
C
  400     CONTINUE
C
C
  500 CONTINUE
C
          AVGPERM = TTLPERM / NDATA
          WRITE(6,1111) TTLPERM, NDATA, AVGPERM
          WRITE(7,1111) TTLPERM, NDATA, AVGPERM
C
C
C
C
C
C
C
C ****************************************************************
C
C FORMAT STATEMENTS
C
C ****************************************************************
C
 1000 FORMAT(1H1,//2X,'BKCALC RESULTS FOR CONVENTIONAL HS ',
     &          'MEASUREMENTS ON CORE PLUG ID -- ',5A10,
     &          //10X,'NUMBER OF DATA SETS          =',I5,
     &          /10X,'CORE PLUG DIAMETER (CM)      =',G12.5,
     &          /10X,'CORE PLUG LENGTH (CM)        =',G12.5,
     &          /10X,'X-SECTIONAL AREA (CM**2)     =',G12.5,
     &          //10X,'IMODE =',I3,/10X,'IMETH =',I3)
 1100 FORMAT(1H1,//2X,'BKCALC RESULTS FOR FIELD PERMEAMETER ',
     &          'MEASUREMENTS ON CORE PLUG ID -- ',5A10,
     &          //10X,'NUMBER OF DATA SETS          =',I5,
     &          /10X,'TIP SEAL RADIUS (IR-CM)      =',G12.5,
     &          /10X,'GEOMETRICAL FACTOR           =',G12.5,
     &          /10X,'X-SECTIONAL AREA (CM**2)     =',G12.5,
     &          /10X,'IMODE =',I3,/10X,'IMETH =',I3)
 1111 FORMAT(1H1,//2X, G16.5, G16.5,
     &          //2X, 'THE AVERAGE PERMEABILITY IS = ', G16.5)
 2000 FORMAT(///2X,'SET NO.',3X,'IMETER',5X,'FLOW RATE (%FS)',3X,
     &          'DELP (PSIG)',5X,'PINV (1/ATM)',3X,'A-PERM (MD)',5X,
     &          'X (CP-SEC)',3X,'Y (ATM-SEC/CM)**2')
 2100 FORMAT(///2X,'SET NO.',3X,'IMETER',5X,'FLOW RATE (%FS)',3X,
     &          'DELP (PSIG)',5X,'PINV (1/ATM)',3X,'A-PERM (MD)',5X,
     &          'X (CM**2/SEC)',3X,'Y (ATM**2-SEC/CM)')
 2200 FORMAT(///2X,'SET NO.',3X,'IMETER',5X,'FLOW RATE (%FS)',3X,
     &          'DELP (PSIG)',5X,'PINV (1/ATM)',3X,'A-PERM (MD)',5X,
     &          'X (1/SEC)',5X,'Y (ATM**2-SEC/CM**3)')
 2300 FORMAT(///2X,'SET NO.',3X,'IMETER',5X,'FLOW RATE (%FS)',3X,
     &          'DELP (PSIG)',5X,'PINV (1/ATM)',3X,'A-PERM (MD)',5X,
     &          'X AND Y NOT FORMULATED YET')
 3000 FORMAT(///2X,'SET NO.',5X,'FLOW RATE (CM**3/SEC)',3X,
     &          'DELP (PSIG)',5X,'PINV (1/ATM)',3X,'A-PERM (MD)',5X,
     &          'X (CP-SEC)',3X,'Y (ATM-SEC/CM)**2')
```

```
3100 FORMAT(///2X,'SET NO.',5X,'FLOW RATE (CM**3/SEC)',3X,
     &        'DELP (PSIG)',5X,'PINV (1/ATM)',3X,'A-PERM (MD)',5X,
     &        'X (CM**2/SEC)',3X,'Y (ATM**2-SEC/CM)')
3200 FORMAT(///2X,'SET NO.',5X,'FLOW RATE (CM**3/SEC)',3X,
     &        'DELP (PSIG)',5X,'PINV (1/ATM)',3X,'A-PERM (MD)',5X,
     &        'X (1/SEC)',5X,'Y (ATM**2-SEC/CM**3)')
3300 FORMAT(///2X,'SET NO.',5X,'FLOW RATE (CM**3/SEC)',3X,
     &        'DELP (PSIG)',5X,'PINV (1/ATM)',3X,'A-PERM (MD)',5X,
     &        'X AND Y NOT FORMULATED YET')
4000 FORMAT(3X,I3,6X,I3,9X,G12.5,4X,G12.5,5X,G12.5,2X,G12.5,
     &        3X,G12.5,6X,G12.5)
4500 FORMAT(3X,I3,12X,G12.5,7X,G12.5,5X,G12.5,2X,G12.5,
     &        3X,G12.5,6X,G12.5)
5000 FORMAT(5A10)
C
9000 FORMAT(1X,G16.5)
C
     STOP
     END
```

APPENDIX II

SCREEN DISPLAYS FOR EXECUTIVE LEVEL CONTROL OF THE ELECTRONIC FIELD PERMEAMETER

```
                        Main Menu

Select one of the following Function Keys:

F1  -  Power up Checklist
              F2  -  Help Menu
              F3  -  Instrument Control Parameters
              F4  -  Calibration Options
              F5  -  Sampling Options
              F6  -  Data Manipulation
              F7  -  System Status
              F8  -  Measurement Control Screen
```

Instrument Control Parameters

Options                                               Current Status

■ Set Mass Flow Rate (% of FS):              Active    Set Point

Mass Flow Meter A   (10 slpm)   ■   80%

Mass Flow Meter B   (1000 sccm)   ■   45%

Mass Flow Meter C   (100 sccm)   ☐

Mass Flow Meter D   (10 sccm)   ☐

☐ User Supplied Settings:    A  B  C  D

Read Mass Meter   ☐ ☐ ☐ ☐

Read Pressure Transducer   ☐ ☐ ☐ ☐

☐ Automatic Settings:

Set Mass Meter (80% FS)   ☐ ☐ ☐ ☐

Read Pressure Transducer   ☐ ☐ ☐ ☐

| F1=Main | F2=Help | F3=Previous | F4=Calibration |
| F5=Sampling | F6=Data | F7=System | F8=Control |

---

Calibration

Options

☐  Measure and Reset Internal Line Loss Curve  (5 min)

-- Open flow, Hoses connected, Meters A & B active

■  Set Linear Calibration Parameters   A B C D

☐ Mass Flow Meter   ☐ ☐ ☐ ☐

■ Pressure Transducer   ☐ ☐ ☐ ☐

☐  Set Tabular Calibration Parameters   A B C D

☐ Mass Flow Meter   ☐ ☐ ☐ ☐

☐ Pressure Transducer   ☐ ☐ ☐ ☐

| F1=Main | F2=Help | F3=Settings | F4=Previous |
| F5=Sampling | F6=Data | F7=System | F8=Control |

Sampling Methods

Options
- ☐ Create new random sampling data set
- ☐ Create new stratified random sampling data set
- ■ Create new transect sampling data set
- ☐ Create new grid sampling data set
- ☐ Create new core plug data set
  - ☐ Conventional    ☐ Unconfined Name of Data Set __Tran1__
Number of Points __1320__

Core Plug Dimensions

OD _____ L _____
☐ mm  ☐ cm

Grid or Transect Parameters

|  | ■ X | ☐ Y |
|---|---|---|
| Origin | 0.0000 | 30.125 |
| Number | 3120 |  |
| Spacing | 5.0000 |  |
| | ☐ mm  ■ cm  ☐ m | |

---

Measurement Control Screen

Data Set Name __Tran1x__   (Transect Sampling)

Point Location for measurement number __00328__

X __328.00__ (mm)    column __00328__
Y __30.125__ (mm)    row    __00001__

Auto
■ Yes
☐ No

Mass Meter Setting (%FS) __80.0__
☐ A   ☐ B   ■ C   ☐ D
Pressure Reading (psig) __14.3697__
☐ A   ■ B   ☐ C   ☐ D
Apparent Permeability (md) __374.25__

G(b/a) __0.9163__    Tip Seal:
Alpha __1.3 e+04__   a(mm) __0.255__
Beta  __25.675__     b(mm) __0.375__

Status

Memory (bytes)
__4754__

ETL (min : sec)
__78 : 35__

Core Dimensions:
OD(mm) __2.4955__
L (mm) __4.1675__

| F1=Attach Note | F2=Return | F4=Review | F5=Next |
| F5=Duplicate | F6=Redo | F7=Stop | F8=GO |

Attach a Note

☐ New Note
■ Modify Existing Note
☐ Replace Existing Note

---

Type Note or Modifications Here (Limit 256 Characters):
<u>This is an Existing Note. Modifications to this note may be</u>
<u>made by simply adding alphanumeric characters to the end</u>
<u>of note. Lists may also be formed:</u>
<u>     (1) Like this</u>
<u>     (2) And this</u>
<u>or (1) this, (2) that and (3) the other thing. The limiting # of</u>
<u>characters for a given note needs to be shown.</u>

---

F1=Main     F2=Help    F3=Settings    F4=Calibration
F5=Sampling    F6=Data    F7=System    F8=Return

---

Data Scan, Transfer and Manipulation

Options
☐ List Currently Available Data Sets
☐ Scan Measurements in One of the Available Data Sets
☐ Save Available Data Set to Tape
☐ Read Data Set from Tape to Memory
☐ Send Data Set to Modem Port
☐ Capture Data Set from Modem Port Name of Data Set _____

---

F1=Main     F2=Help    F3=Settings    F4=Calibration
F5=Sampling    F6=Previous    F7=System    F8=Control

| System Status | | | | |
|---|---|---|---|---|
| Power Supply | -- | Current Supply Voltage (DC) | | 11.85 |
| | ■ Nicad / Cell Powerpack | | ETL (min) | 73.4 |
| | ☐ AC / DC Recharge Adapter | | | |
| ICU Status | -- | Available RAM (bytes) | | 4357 |
| | ■ All Channels Active | | Reset Warning Flags | |
| | ☐ | | ☐ Yes    ■ No | |

| Meters | Mass Flow | Status | Pressure | Status |
|---|---|---|---|---|
| A | 0-10 slpm | ☐ | 0-10 psid | ■ |
| B | 0-1000 sccm | ■ | 0-50 psid | ■ |
| C | 0-100 sccm | ■ | 0-200 psid | ■ |
| D | 0-10 sccm | ☐ | | ☐ |

| F1=Main | F2=Help | F3=Settings | F4=Calibration |
|---|---|---|---|
| F5=Sampling | F6=Data | F7=Previous | F8=Control |

What is claimed is:

1. A method of measuring the permeability of a rock formation in the filed by operating a portable minipermeameter; said minipermeameter including a source of pressurized gas; a manually positionable injection tip including a resilient sealing member for directing said pressurized gas to flow into said rock formation; a portable instrument package connected to said injection tip via a flexible hose, said portable instrument package including at least one electronic flow controller connected in series between said source of pressurized gas and said hose for adjusting the rate of flow of said gas into said rock formation, and at least one electronic pressure sensor connected to said hose for sensing the pressure of said gas flowing into said rock formation; and a microcomputer system having an input device for receiving a command from an operator to initiate the performance of a permeability measurement upon said rock formation, an input device for reading the pressure sensed by said electronic pressure sensor, an output device for operating said flow controller, and output means for signalling that a permeability measurement has been completed and indicating a calculated permeability value to said operator, and a memory storing a control procedure executable by said microcomputer system for responding to said command by successively operating said electronic flow controller to set said rate of flow to a predetermined value, reading the pressure sensed by said electronic pressure sensor when approximately steady-state is reached, operating said output means to signal the operator when the pressure sensed by said electronic pressure sensor is read, operating said electronic flow controller to restrict the flow of gas to conserve said pressurized gas between permeability measurements, calculating the permeability of the rock formation from said predetermined value of flow and said pressure having been read from said electronic pressure sensor, and operating said output means to indicate the calculated value of permeability to said operator; said method comprising the steps of:

(a) manually positioning said injection tip at a selected location on said rock formation and manually pressing said resilient sealing member into contact with a surface of said rock formation at said selected location;

(b) operating said input device to enter said command to initiate the performance of a permeability measurement;

(c) removing said resilient sealing member from said surface of said rock formation when said output means indicates that the permeability measurement has been completed; and (d) viewing the calculated value of permeability indicated by said output means.

2. The method as claimed in claim 1 wherein said microcomputer system calculates the permeability of the rock formation by applying a form of Darcy's law including a geometrical factor (G) which depends upon the particular shape of the injection tip.

3. The method as claimed in claim 1 wherein said input device for receiving said command from said operator is a switch mounted near said injection tip, and said output means includes a beeper for emitting an acoustic signal to indicate that the permeability measurement has been completed.

4. The method as claimed in claim 1, wherein said microcomputer system determines when said pressure assumes approximately a steady state value by repetitively reading said pressure.

5. The method as claimed in claim 1, wherein said microcomputer system includes a first microcomputer that operates said flow controller and reads the pressure sensed by said electronic pressure sensor, and a second microcomputer that receives said command from said operator, calculates the value of the permeability of the rock formation, and operates said output means to signal when the permeability measurement has been completed and to indicate the calculated permeability value to the operator.

* * * * *

UNITED STATES PATENT AND TRADEMARK OFFICE
CERTIFICATE OF CORRECTION

PATENT NO. : 4,864,845
DATED : September 12, 1989
INVENTOR(S) : Mark A. Chandler et al.

It is certified that error appears in the above-identified patent and that said Letters Patent is hereby corrected as shown below:

In the Abstract, line 20, after "sensing" please insert ",".

In Col. 4, line 68, please change "22" to --42--.

In Col. 9, line 9, please change "cm" to --$cm^3$--.

In Col. 9, line 19, please change "a" to --$\underline{a}$--.

In Col. 9, line 20, please change "b" to --$\underline{b}$--.

In Col. 9, line 32, the equation should read:

$$G(b_D, R_D, L_D) = 2\pi \int_0^1 \left\{ \frac{\partial m_D}{\partial z_D} \right\}_{z_D = 0} r_D dr_D$$

In Col. 9, line 57, after "to" please insert ":".

In Col. 9, line 48, please change "a" to --$\underline{a}$--.

In Col. 9, line 48, please change "b" to --$\underline{b}$--.

In Col. 12, line 3, after "7" please insert --)--.

In Col. 12, line 34, please change "," to --'--.

UNITED STATES PATENT AND TRADEMARK OFFICE
CERTIFICATE OF CORRECTION

PATENT NO. : 4,864,845

DATED : September 12, 1989

INVENTOR(S) : Mark A. Chandler et al.

It is certified that error appears in the above-identified patent and that said Letters Patent is hereby corrected as shown below:

In Col. 12, line 40, please change "permeameter s" to --permeameter's--.

In Col. 12, line 65, after ""I"" please insert --.--.

In Col. 13, line 43, please change "sep" to --step--.

In Col. 13, line 48, please change "," to --'--.

In Col. 13, line 59, before " If" please insert --.--.

In Col. 14, line 51, after ""NN"" please insert --.--.

In Col. 15, line 66, before "J"" please insert --"--.

In Col. 33, line 34, please change "filed" to --field--.

In Col. 33, line 62, before "steady-state" please insert "a".

Signed and Sealed this

Sixteenth Day of October, 1990

Attest:

HARRY F. MANBECK, JR.

Attesting Officer

Commissioner of Patents and Trademarks